(12) United States Patent
Jung et al.

(10) Patent No.: US 8,073,535 B2
(45) Date of Patent: Dec. 6, 2011

(54) RADIANT ENERGY DERIVED TEMPERATURE(S)

(75) Inventors: Edward K. Y. Jung, Bellevue, WA (US);
Eric C. Leuthardt, St Louis, MO (US);
Royce A. Levien, Lexington, MA (US);
Robert W. Lord, Seattle, WA (US);
Mark A. Malamud, Seattle, WA (US);
John D. Rinaldo, Jr., Bellevue, WA (US); Lowell L. Wood, Jr., Livermore, CA (US)

(73) Assignee: Invention Science Fund 1

( * ) Notice: Subject to any disclaimer, the term of this patent is extended or adjusted under 35 U.S.C. 154(b) by 939 days.

(21) Appl. No.: 11/490,490

(22) Filed: Jul. 19, 2006

(65) Prior Publication Data

US 2008/0021344 A1    Jan. 24, 2008

(51) Int. Cl.
*A61B 5/00*     (2006.01)
*A61B 5/103*    (2006.01)
*A61B 5/117*    (2006.01)
*G08B 23/00*    (2006.01)
*G08B 17/12*    (2006.01)

(52) U.S. Cl. ........ 600/547; 600/587; 600/595; 340/501; 340/573.7; 340/600

(58) Field of Classification Search ................... 600/549, 600/595, 587; 340/501, 573.7, 600
See application file for complete search history.

(56) References Cited

U.S. PATENT DOCUMENTS

| | | | |
|---|---|---|---|
| 4,525,885 A * | 7/1985 | Hunt et al. | 5/713 |
| 4,944,060 A * | 7/1990 | Peery et al. | 5/713 |
| 5,109,560 A * | 5/1992 | Uetake | 5/713 |
| 5,542,136 A * | 8/1996 | Tappel | 5/710 |
| 6,646,556 B1 * | 11/2003 | Smith et al. | 340/573.1 |
| 6,897,781 B2 * | 5/2005 | Cooper et al. | 340/573.1 |
| 6,987,232 B2 * | 1/2006 | Smith et al. | 200/85 R |
| 7,030,764 B2 * | 4/2006 | Smith et al. | 340/573.1 |
| 7,278,179 B2 * | 10/2007 | Schneider | 5/714 |
| 7,340,293 B2 * | 3/2008 | McQuilkin | 600/474 |
| 7,377,935 B2 * | 5/2008 | Schock et al. | 607/104 |
| 7,378,975 B1 * | 5/2008 | Smith et al. | 340/573.1 |
| 7,397,380 B1 * | 7/2008 | Smolsky | 340/573.1 |
| 7,480,951 B2 * | 1/2009 | Weismiller et al. | 5/600 |
| 2004/0046668 A1 * | 3/2004 | Smith et al. | 340/573.7 |
| 2004/0189475 A1 * | 9/2004 | Cooper et al. | 340/573.1 |
| 2005/0011738 A1 * | 1/2005 | Smith et al. | 200/85 R |

(Continued)

FOREIGN PATENT DOCUMENTS

JP    04106353 A  *  4/1992

(Continued)

OTHER PUBLICATIONS

Crenshaw, BS, Ryan P.; Vistnes, MD, Lars M.; "A decade of pressure sore research: 1977-1987"; Veterans Administration, Journal of Rehabilitation Research and Development; bearing a date of Winter 1989; pp. 63-74; vol. 26; No. 1.

(Continued)

*Primary Examiner* — Max Hindenburg
*Assistant Examiner* — Sean Dougherty

(57) ABSTRACT

One aspect relates to adjusting a positional state of an individual to a physiological aspect of the individual at least partially in response to detecting a radiant kinetic energy from the individual. Another aspect relates to indicating to configure an individual at least partially in response to a determining at least one physiologically-indicating body temperature of the individual derived at least partially based on a detecting a radiant kinetic energy from the individual.

51 Claims, 12 Drawing Sheets

U.S. PATENT DOCUMENTS

| | | | | |
|---|---|---|---|---|
| 2005/0172398 | A1* | 8/2005 | Smith et al. | 5/81.1 R |
| 2005/0262639 | A1* | 12/2005 | Butler | 5/713 |
| 2006/0069418 | A1* | 3/2006 | Schock et al. | 607/104 |
| 2007/0056101 | A1* | 3/2007 | Mahajan et al. | 5/600 |
| 2007/0163043 | A1* | 7/2007 | Lemire et al. | 5/600 |
| 2007/0164871 | A1* | 7/2007 | Dionne et al. | 340/573.1 |
| 2007/0174964 | A1* | 8/2007 | Lemire et al. | 5/600 |
| 2007/0174965 | A1* | 8/2007 | Lemire et al. | 5/600 |
| 2008/0077020 | A1* | 3/2008 | Young et al. | 600/484 |
| 2008/0120784 | A1* | 5/2008 | Warner et al. | 5/658 |
| 2009/0275808 | A1* | 11/2009 | DiMaio et al. | 600/301 |

FOREIGN PATENT DOCUMENTS

JP 2003102793 A * 4/2003

OTHER PUBLICATIONS

Hobson, Ph.D.; Douglas A.; "Principles of Pressure Management"; Wheelchairnet.org; printed on Jul. 11, 2006; pp. 1-13; located at http://www.wheelchairnet.org/wcn_wcu/SlideLectures/DAH/PM_html/PPT.html.

"Mammography/Thermography/Ultrasound What's The Difference?"; Breastthermography.com; bearing dates of May 19, 2006 and 1998-2005; printed on Jul. 11, 2006; pp. 1-3; located at http://www.breastthermography.com/mammography_thermography.htm.

"OS-XL, Thermal Imaging Thermometer OMEGASCOPE® OS-XL"; Omega.com; bearing a date of 2006; printed on Jul. 11, 2006; pp. 1-4; located at http://www.omega.com/pptst/OS-XL.html.

"Overview of Mikron's IR Sensors, Imaging Pyrometers, Thermal Imaging and Calibration Instrumentation"; Techsavvy.com; printed on Jul. 11, 2006; pp. 1-6; located at http://www.techsavvy.com/industry/file/national/08f98/mkr16.html?id=122077&comp_id=08F98&base_region=*.

"Patient Alarms—Fall Reduction Tools Alerting Risks, What is a Patient Alarm"; uCanHealth.com; bearing a date of 2004; printed on Jun. 19, 2006; pp. 1-2; located at http://ucanhealth.com/patient_alarm.htm.

"SARS Temperature Sensors"; Temperatures.com; bearing a date of 2003-2004; printed on Jun. 19, 2006; pp. 1-7; located at http://www.temperatures.com/sarssensors.html.

Saunders, Peter; "An Imaging Radiation Thermometer"; pp. 1-6; located at http://msl.irl.cri.nz/training_&_resources/Measurement_articles/ImagRadTherm.pdf.

Schulman, Joseph H.; "Stimulating and Sensing Network Inside the Human Body"; bearing a date of 2006; printed on Jun. 19, 2006; pp. 1-2; located at http://csdl2.computer.org/persagen/DLAbsToc.jsp?resourcePath=/dl/proceedings/bsn/&toc=comp/proceedings/bsn/2006/2547/00/2547toc.xml&DOI=10.1109/BSN.2006.52.

"Sensing body heat—Wip—Brief Article—Product/Service Evaluation"; Findarticles.com; bearing dates of Nov. 2003, 2003, and 2004; printed on Jun. 19, 2006; pp. 1; located at http://www.findarticles.com/p/articles/mi_m0KJI/is_11_115/ai_111064200/print.

Stephenson, Mary Ellen; "Fawcett researches pressure problems for surgical patients"; Indiana.edu; bearing dates of May 13, 2005 and 2003; printed on Jul. 11, 2006; pp. 1-2; located at http://www.indiana.edu/~ocmhp/051305/text/surgical.shtml.

"What is Breast Thermography"; Breastthermography.com; bearing dates of Apr. 21, 2006 and 1998-2005; printed on Jul. 11, 2006; pp. 1-4; located at http://www.breastthermography.com/breast_thermography_mf.htm.

Foy, Paul; "IBM to Provide Network to Monitor Cattle"; Physorg.com; bearing dates of Aug. 25, 2006, 2003-2006 and 2006; printed on Aug. 28, 2006; pp. 1-3; located at http://www.physorg.com/news75712508.html.

U.S Appl. No. 12/803,112, Jung et al.

* cited by examiner

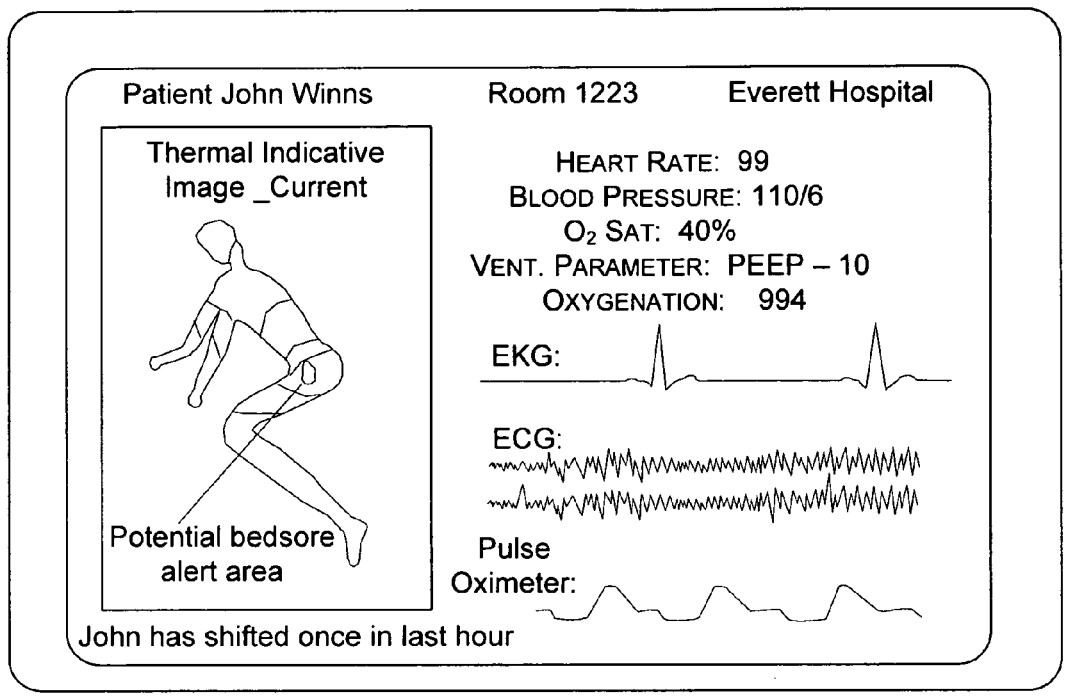
FIG. 9
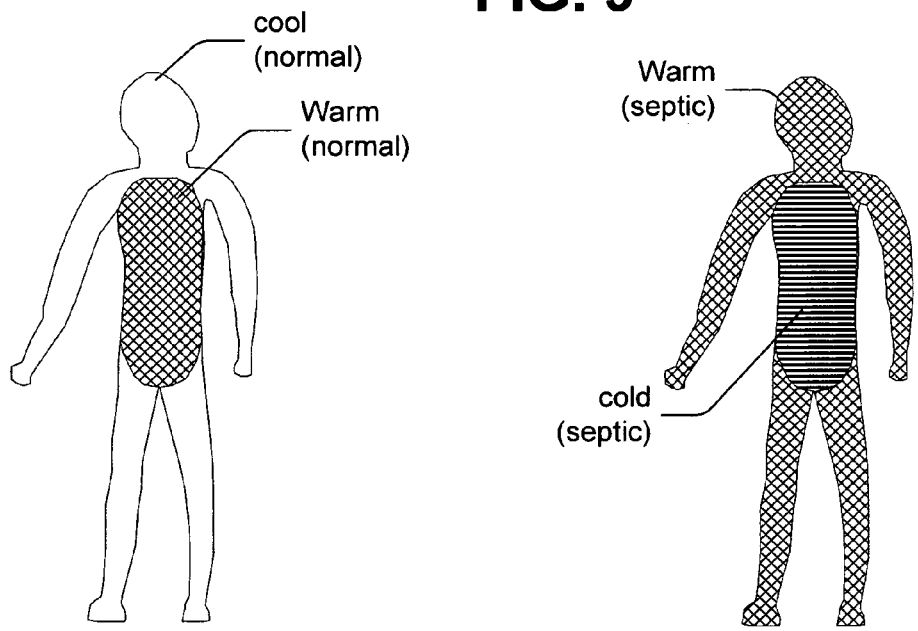
FIG. 10a  FIG. 10b

RADIANT ENERGY DERIVED TEMPERATURE(S)

TECHNICAL FIELD

Certain aspects of this disclosure can relate to, but are not limited to, radiant kinetic energy imagers and/or techniques.

BRIEF DESCRIPTION OF THE FIGURES

FIG. 7, including

FIG. 9 is a diagram of one embodiment of an illustrative individual imager that can include the radiant kinetic energy imager;

FIG. 10 (including FIGS. 10a and 10b) is a diagram of images that can be produced by the radiant kinetic energy imager;

FIG. 13, including

FIG. 14, including

DETAILED DESCRIPTION

Figure 1:
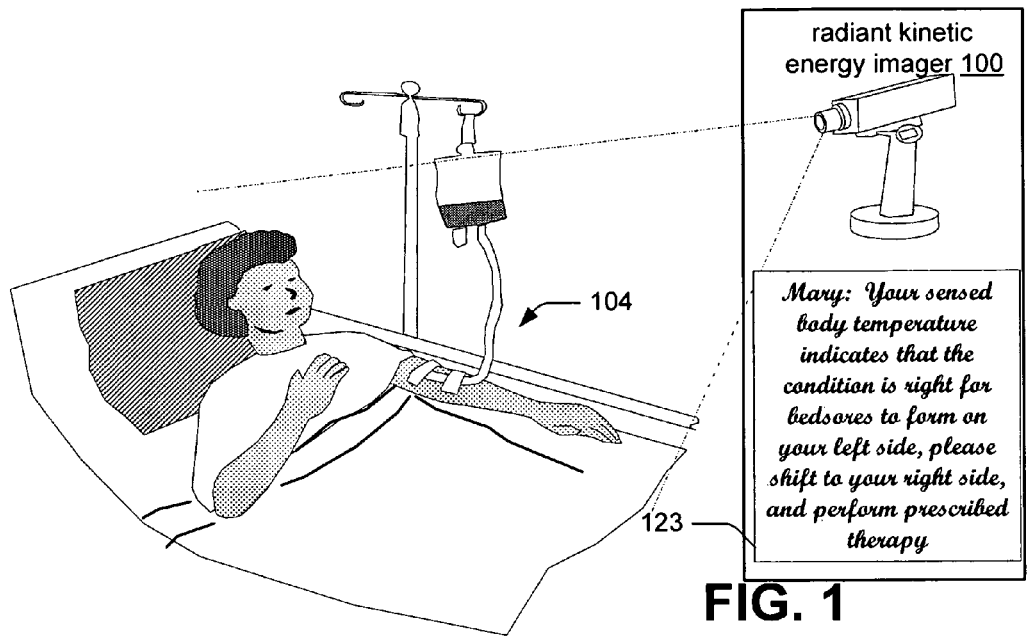
FIG. 1 is a diagram of one embodiment of a radiant kinetic energy imager as being applied to an individual who is a human.

At least certain portions of the text of this disclosure (e.g., claims and/or detailed description and/or drawings as set forth herein) can support various different claim groupings and/or various different applications. Although, for sake of convenience and understanding, the detailed description can include section headings that may generally track various different concepts associated with claims or general concepts contained therein, and is not intended to limit the scope of the invention as set forth by each particular claim. It is to be understood that support for the various applications or portions thereof thereby can appear throughout the text and/or drawings at one or more locations, irrespective of the section headings.

1. Certain Embodiments of a Body Radiant Kinetic Energy Imager

Certain embodiments of this disclosure can relate to utilizing at least one radiant kinetic energy imager 100 as described with respect to FIGS. 1 to 4 that can be utilized to recognize radiant kinetic energy being produced by an individual 104. Certain embodiments of the at least one radiant kinetic energy imager 100 can thereupon, depending upon context, adjust a positional state of an individual or alternatively configure the individual. The temperature of the individual 104 at one or more locations can thereupon be ascertained based on the detected radiant kinetic energy. Thereafter, the temperature in the room, bed, chair, or other environmental location of the individual can be adjusted or controlled, or some other action can be provided with respect to the individual 104 based at least in part based on the radiated kinetic energy that is being produced by the individual 104 and/or their environment.

Within this disclosure, certain embodiments of the radiated kinetic energy can, depending on context, indicate a radiant kinetic energy emitted from the individual. Certain embodiments of the radiant kinetic energy emitted from the individual can provide at least some information that can indicate, in general, certain health, circulatory, or other aspects of the individual. Certain embodiments of the radiant kinetic energy imager 100 can indicate, for example, certain health, circulatory, or other aspects of the individual as taken across a sizeable area of the individual, (as compared to one or two locations), and certain radiant kinetic energy imagers can even create a thermal map or image as described in this disclosure with respect to FIGS. 5, 6, 9, 10a, and/or 10b. Certain embodiments of the radiated kinetic energy of the individual can be utilized to derive significant information about the individual that may not be discernible based on a localized temperature of the individual as may be obtained by certain conventional thermometers.

Certain embodiments of the radiant kinetic energy imager 100 can be configured to operate in a manner that can limit contact with the individual. Consider, for example, that the temperature of the individual can be imaged in a hallway, office, waiting room, or other location when the individual is sitting, walking, standing, resting, etc., such as in a hallway, examination room, or waiting room that may be, for example, to view a medical personnel. Certain embodiments of the radiant kinetic energy imager 100 can be configured to operate relatively unobtrusively such as the individual may or may not be aware of the particular location of the radiant kinetic energy imager. Since certain embodiments of the radiant kinetic energy imager 100 can be configured to operate in a manner involving less contact and/or less obtrusively with respect to the individual than traditional thermometers, the temperature of the individual can be taken more frequently. Certain embodiments of the radiant kinetic energy imager can even be configured to allow the temperature of a number of individuals to be taken, when in a supposedly relatively healthy state, such as may be used to more closely monitor the health of even healthy individuals reporting to work, traveling, etc.

Certain embodiments of the radiant kinetic energy imager 100 can, depending upon context, thereupon adjust a positional state of the individual based at least in part on a detected radiated kinetic energy from the individual. Consider, for example, that with certain automated embodiments of the radiant kinetic energy imager 100, the individual could be re-positioned, alerted to position themselves, cooled, tilted, shifted, etc. into another positional state based at least in part on the detected radiated kinetic energy from the individual. Certain embodiments of the adjusting the positional state can have a variety of affects that can vary from allowing the individual to move, to wake up a body part of the individual with poor circulation, to shifting the individual to perhaps improve the circulation of the individual, to improve blood flow and/or associated oxygen flow to bodily parts of the individual, to position those individuals who are unable to move and/or are unaware that they should move to limit poor circulator aspects such as bed sores, illness or injuries due to poor circulation, etc.

Figure 2:
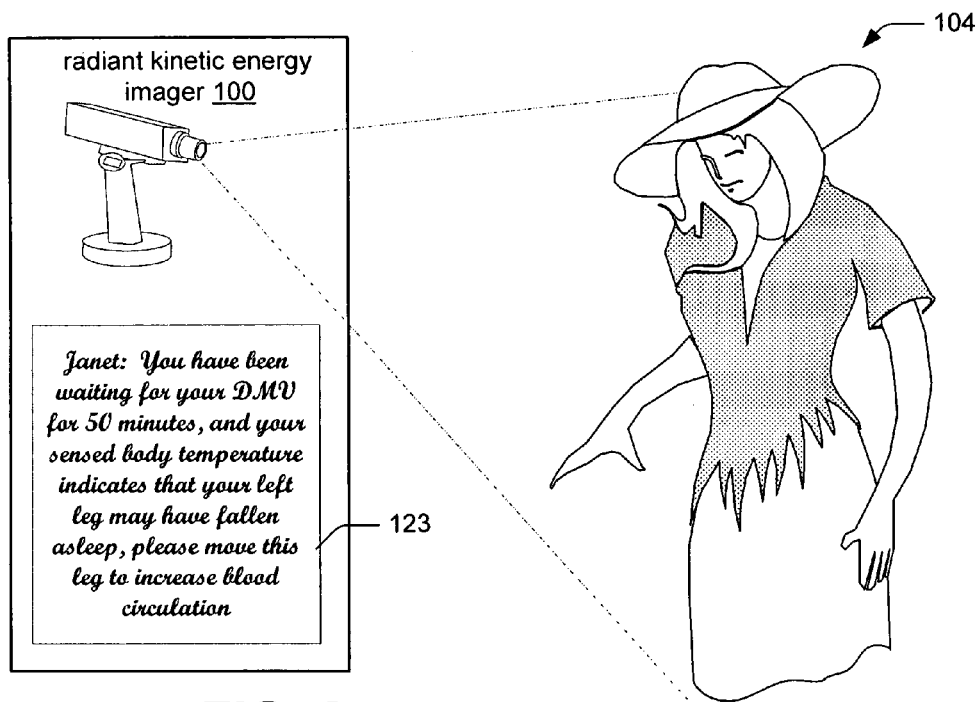
FIG. 2 is a diagram of another embodiment of a radiant kinetic energy imager as being applied to another individual who is a human.
Figure 3:
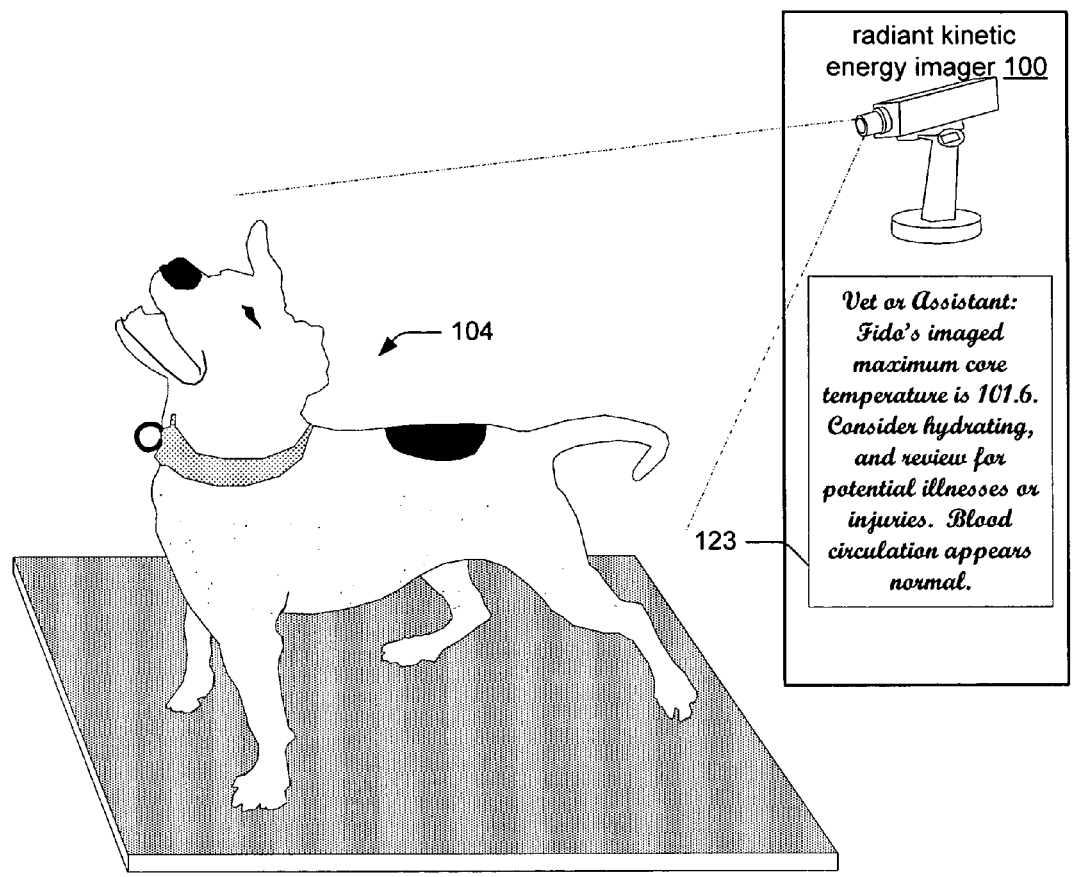
FIG. 3 is a diagram of another embodiment of a radiant kinetic energy imager as being applied to yet another individual which is an animal.

FIGS. 1 to 3, for example, illustrate three embodiments of individual prompts or positioning mechanism 123, which may be configured as a portion of the radiant kinetic energy imager 100, which indicates to the individual, an attendant, or a caretaker of some action that can be performed based at least in part on the sensed radiated kinetic energy. While the individual prompts or positioning mechanism 123 are intended to be illustrative in nature, and not limiting in scope, it is intended that the radiant kinetic energy imager 100 can include a mechanism that indicates to the individual, a caretaker, or an attendant (or alternately performs some action itself) which adjusts the individual such as by positioning the individual. For example, varied embodiments of the individual prompts or positioning mechanism 123 can "automatically" reposition the individual such as by shifting them, provide a text, written or GUI-based message, provide a recorded or audio message, etc., as appropriate considering, among other factors, the particular individual and their state or condition.

Certain embodiments of the radiant kinetic energy imager 100, by definition, may be configured to detect radiated kinetic energy, and certain embodiments may not require an interrogatory signal, radiation source, etc., and instead may operate at least partially by detecting the emitted radiation. Certain embodiments of the radiant kinetic energy imager 100 as described in this disclosure, can also utilize emitted electromagnetic radiation, etc., to locate at least a part of the imaging of the individual, etc. which positional information can thereupon be utilized to image a desired individual or location(s) of the individual utilizing the radiated kinetic energy. As such, while this disclosure uses the term "radiant kinetic energy imager", it is to be understood that other mechanisms, forms of electromagnetic radiation, transmission mechanisms, etc. can be utilized in combination therewith to affect its imaging and/or operation.

Certain embodiments of the radiant kinetic energy imager 100 can utilize a variety of logic to operate that may relate, for example, to its operation and association with particular individuals. For example, certain embodiments of the radiant kinetic energy imager 100 can be configured to monitor all individuals entering a building, region, etc. that can be actuated as any individual enters the monitoring and/or detection area, to consider whether any of the individuals have a highly raised temperature, such as may be associated with an illness, sickness, injury, etc. Other embodiments of the radiant kinetic energy imager 100 can be configured to operate with a group or number of individuals, such as those patients of a hospital, doctor, or clinic, that can configured to be operated when any of the desired individuals is within a detecting region.

Figure 8:
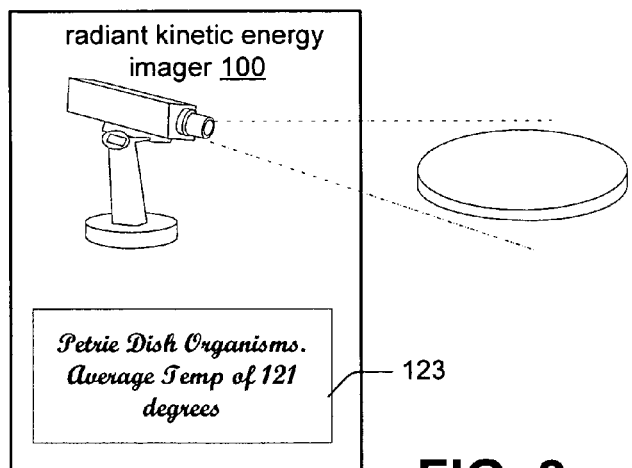
FIG. 8 is a diagram of another embodiment of a radiant kinetic energy imager as being applied to yet another individual which is an organism.

Within this disclosure, the term "individual" which is referenced as 104 can include, depending on context, but may not be limited to, humans such as described with respect to FIGS. 1 and 2, animals such as described with respect to FIG. 3, or organisms as described with respect to FIG. 8. A number of individuals 104 as described in this disclosure may relate to nursing home patients, immobile persons, handicapped individuals, individuals visiting doctors or clinics, etc.

Within this disclosure, the term "individual" 104 may be generally segmented into two general types to thereby modify the application of certain embodiments of the radiant kinetic energy imager: those individuals 104 that are generally unhealthy as described with respect to FIG. 1 and/or those individuals that are generally healthy, as described with respect to FIG. 2. This differentiation between healthy and unhealthy individuals should be considered as a general guideline, largely because there may be a considerable amount of disagreement or misunderstanding in both the medical and legal areas as to which individuals are to be considered as healthy and which are to be considered as unhealthy.

Within this disclosure, certain embodiments of the unhealthy group of individuals 104 such as may be monitored by certain embodiments of the radiant kinetic energy imager 100 may be considered, depending on context, as those individuals 104 that may be unable to detect or respond to their unusual body temperature such as may, for example, require that the individual(s) position themselves, or alternately the individual(s) be positioned by others.

Certain unhealthy individuals 104 (e.g., of the human or animal varieties) that may utilize certain embodiments of the radiant kinetic energy imager 100 may, e.g., be unconscious, medicated, paraplegic, quadriplegic, infirm, comatose, mentally challenged, and/or somehow otherwise require additional help to ascertain or monitor their condition, or to position themselves, etc. Within this disclosure, certain embodiments of the healthy individuals that may utilize certain embodiments of the radiant kinetic energy imager 100 may be those individuals that can position themselves relatively easily.

Certain embodiments of the radiant kinetic energy imager 100 can monitor, treat, or maintain patients with spinal cord injuries, and other intensive care patients who cannot move. For example, after some temperature in the individual is sensed as being below a desired level (indicative of, for example, a reduced blood flow), certain embodiments of the radiant kinetic energy imager 100 can thereupon move or position the patient, while other embodiments of the radiant kinetic energy imager 100 can indicate the individual should be moved or positioned. Certain embodiments of the radiant kinetic energy imager 100 can involve infrared sensors (or other types of radiant kinetic energy detectors) that may be positioned adjacent to the individual, within the bed which the individual is situated, etc. Other types of thermal sensors that can sense the radiated heat from the individual can also be used in certain embodiments of the radiant kinetic energy imager 100. Certain embodiments of the radiant kinetic energy imager 100 can, depending upon operation and/or configuration, detect a radiated kinetic energy, which may represent a full-global, a regional, or a partial temperature as may be taken across a considerable area of the individual.

Certain individuals 104, who may be monitored by certain embodiments of the radiant kinetic energy imager 100, may be considered, depending on context, as those individuals 104 who for a variety of reasons may be unaware that certain portions of their body are not getting proper blood flow. Certain embodiments of the radiant kinetic energy imager 100 can, with relatively "normal" or "healthy" patients, monitor the temperature of the individual as their temperature varies when they are resting, inactive, or active. Consider, for example, that certain embodiments of the radiant kinetic energy imager 100 can be applied to individuals on aircraft flights, car, bus, truck, or train rides (especially those that are long in duration), movies, waiting rooms, offices, etc. As such, certain embodiments of the radiant kinetic energy imager 100 can operate non-invasively, and thereby be more utilized for preventative medical purposes, etc.

While a considerable number of the radiant kinetic energy imager 100 as described in this disclosure may be configured to be applied to clinical applications, there are envisioned to be a variety of embodiments of the radiant kinetic energy imager that may be directed to non-clinical applications, such as maintaining the temperature of a home, office, theater, or other environment of the individual, etc. based at least on a detected temperature of the individual by the radiant kinetic energy imager. As such, the temperature of a bed, chair, couch, area, and/or room in which the individual may be situated can be altered or reconfigured at least partially in response to a sensed temperature of the individual by certain embodiments of the radiant kinetic energy imager 100. Certain embodiments of the radiant kinetic energy imager 100 can be embedded within, integrated into, or otherwise associated with certain embodiments of the environment of the individual (e.g., a bed, couch, room, etc.) such as to provide a temperature-regulatory system for the individual. Certain embodiments of the radiant kinetic energy imager 100 can be associated with individuals, such that the temperature of such individuals as certain drivers, pilots, operators, passengers, occupants, etc. of such vehicles as cars, busses, trains, aircraft, ships, etc. can be monitored. Certain embodiments of the radiant kinetic energy imager 100 can thereby detect a local temperature of a portion of the individual.

Certain individuals 104, such as may be monitored by certain embodiments of the radiant kinetic energy imager 100, may be considered, depending on context, as those individuals who, for a variety of reasons, may be desired to take their temperature, often particularly across a considerable portion of the individual. Consider, for example, that with generally healthy individuals 104 who are visiting a doctor's office, a hospital, or even nursing home; conventional thermometers may be configured to take individuals 104 temperatures orally, rectally, under their arms, or some other location that is intended to be representative of the individuals 104 core temperature. Certain individuals 104 may be uncomfortable about having (or simply not desire to have) their temperature taken with traditional thermometers, for example. Certain versions of such conventional thermometers may be inconvenient, clumsy, embarrassing, and/or uncomfortable for the individual, and/or may provide output of questionable accuracy or from only a limited region of the individual.

Additionally, it may be difficult to take certain individual's 104 temperature using conventional thermometers due to a variety of reasons that may include but are not limited to: illness, injury, unconsciousness or sleep of the individual 104, etc. Consider an instance when the individual is a patient in an operating room, certain embodiments of the radiant kinetic energy imager 100 can be utilized to continually or repetitively monitor the temperature of the individual throughout the operation. Certain embodiments of conventional thermometers may take the temperature at a regionalized location.

Certain embodiments of the radiant kinetic energy imager 100 can image the temperature of the individual across a considerable surface area of the individual's body, which information can be utilized and/or analyzed to, for example, reposition the individual; and can thereupon reduce the formation of "cold spots" or "hot spots" for certain radiated kinetic energy that do not accurately reflect the temperature of the individual. Certain reasons why such cold spots or hot spots using conventional single-point thermometers may include, but is not limited to, malfunction of the conventional thermometer, as well as taking the temperature at a relatively small sample region which is not indicative of more than a very small location of the individual.

In addition, the circulation of certain injured individuals or those having poor circulation, can be monitored to ensure the circulation does not drop to an unhealthy or dangerous level, etc. Certain embodiments of the radiant kinetic energy imager 100 can indicate an aberration of the expected temperature that can be indicative of an injury, illness, lack of circulation, etc. It appears likely that certain clinical embodiments the radiant kinetic energy imager 100 (both when applied to the entire body, regions of the body, or parts of organs of the body) to determine the physiologically-indicating body temperature, when applied to diagnosis or operations, could provide significant information that would be useful for the doctor, the medical personnel, the individual, and/or the treatment or procedure.

Certain embodiments of the radiant kinetic energy imager 100 may thereby be configured to sense the radiant kinetic energy emitted by the individual 104, and certain embodiments at a number of locations across the individual 104 to determine the physiologically-indicating body temperature. It is thereby envisioned that physicians and/or other medical personnel could in a variety of situations ascertain a more complete temperature indication of the individual 104 such as with a radiated kinetic energy than with conventional thermometers (certain embodiments of the conventional thermometer can sense the temperature of the individual 104 at a single location). As such, certain embodiments of the radiant kinetic energy imager 100 can thereby be configured to accurately and completely determine the body temperature of the individual 104. Certain embodiments of the radiant kinetic energy imager 100 can thereupon schedule an appropriate health regimen schedule based at least in part on the sensed radiated kinetic energy.

Certain embodiments of the radiant kinetic energy imager 100 may thereby be applied to certain individuals (e.g., humans or animals) that are incapable or otherwise unable or unwilling to communicate. Providing certain embodiments of the radiant kinetic energy imager 100 to individuals who are animals provides other aspects of the radiant kinetic energy imager 100. It is be understood that certain embodiments of the radiant kinetic energy imager 100 may also suitably be applied to animals as described with respect to FIG. 3 because their inability to communicate. Certain embodiments of the radiant kinetic energy imager 100 may also suitably be applied to animals or organisms as described with respect to FIG. 3 without a necessity to "capture" or "closely confine" the animal or organism. As such, certain embodiments of the radiant kinetic energy imager 100 can be applied to wild animals without the necessity of capturing, medicating, or tranquilizing them; as well as wild or domesticated animals without the necessity to apply some temperature-deriving mechanism that the animal may not wish or object to have applied to them. Consider that certain embodiments of the radiant kinetic energy imager 100 can image the temperature of the animal over a relatively larger area in a relatively unobtrusive manner, with little or no contact with the animal.

As such, by determining a relatively complete analysis of animal's temperature, for example, certain veterinarians or other humans or mechanisms that are treating animals may be able to provide a more complete analysis based upon the radiant energy signature obtained from the animal. It can be envisioned that the animals temperature could be monitored on a more frequent basis. Consider, for example, that wild, livestock, or domesticated animals that are at a veterinarian, a pound, a store, a corral, in transit, in the wild, etc. could have their radiated kinetic energy and/or temperature monitored on a regular basis such as which would be useful to identify ill, sick, injured, contagious, or other animals, and potentially limit the spread of illness among animals at these and other locations.

Certain embodiments of the radiant kinetic energy imager 100 can be applied to a variety of domesticated or wild animals such as dogs, cats, hamsters, guinea pigs, etc., and thereby can limit difficulty in obtaining a temperature of a domesticated animal, but can also limit danger associated with taking temperatures of domesticated animals (e.g., dog bites, scratches, infections, etc.). Certain embodiments of the radiant kinetic energy imager 100 can also be used to detect radiant energy and/or temperature of non-domesticated, livestock, or wild animals. It may be desirable to use certain embodiments of the radiant kinetic energy imager, for example, to monitor the temperature, as well as other temperature-related aspects such as general health, of such zoo, contained, or wild animals as bears, lions, alligators, dogs, raccoons, etc. from remote locations such as to limit human contact with potentially dangerous or infective animals. As such, certain embodiments of the radiant kinetic energy imager 100 can obtain some information that can be utilized to determine the health, condition, state, etc. of wild, zoo, or contained animals, without the associated difficulty or danger of having to capture the animal. Certain embodiments of the radiant kinetic energy imager 100 can thereby be utilized to monitor a variety of health aspects of animals, which may be either wild, livestock, and/or domesticated.

Certain veterinarians, and other people who care for animals, may find it challenging to monitor the temperature of the animals. Certain embodiments of the radiant kinetic energy imager 100 may be applied remotely of the individual 104 such as the animal, such as to limit anxiety or agitation to the animal, as well as resultant potential scratches or even potential injury to those treating the animal. For a reason such as this, temperatures of animals may not be frequently taken, thereby limiting the access of valuable information that may be used to determine the health of the animal. Consider in the instance of wild and/or dangerous animals; in order to take their temperature, such animals may have to initially be captured (which by itself can be dangerous, time consuming, and/or adventuresome).

Certain embodiments of the radiant kinetic energy imager 100 can also detect the radiated kinetic energy of organisms, such as bacteria, cells, viruses, tumors, etc. as described with respect to FIG. 8. To state the obvious, it may not be possible or convenient to determine the temperature of organisms using conventional thermometers. As such, information that may be obtained relating to the temperature of organisms may not be obtained using conventional techniques. Such temperature of organisms can be provided as a base-line, diagnosis, detection and/or other mechanism. Consider that certain healthy bacteria have a particular temperature, determining that the temperature of the bacteria varies considerably from that could be useful in determining that the bacteria or other organism is not healthy, is injured, is dead, or is in some other state. Certain embodiments of the radiant kinetic energy imager 100 can even involve positioning the organism (or indicate how to position the organism) in a desired position. It may, for example, be desired to maintain the organism at a prescribed approximate temperature, or temperature range, and consider how they respond. For example, will raising the temperature of particular cancer cells, bacteria, or viruses or other undesirable organisms tend to make them inactive, or kill them? Will changing the temperature of certain desirable cells by a number of degrees allow them to multiply quicker and/or be healthier? Certain embodiments of the radiant kinetic energy imager 100 can thereby act to monitor characteristics of organisms based on the temperature of the organism themselves, instead of the temperature of the culture or other organism in which the organism(s) is situated. Within this disclosure, the term "organism" can include, but is not limited to, a single organism, at least two similar organisms (e.g., a colony), and/or at least two unlike organisms. In certain embodiments the temperature of the organism or multiple organisms (e.g., all the organisms in a petri dish) can be taken in general using certain embodiments of the radiant kinetic energy imager 100, or alternatively the temperature can be taken across various portions of the organism to provide an indication of a number of organisms, one organism, and/or a portion of the organism.

Certain embodiments of the radiant kinetic energy imager 100 that contain, for example, organisms situated in a culture can involve a technician positioning or shifting the cultures at least partially in response to detected output from the radiant kinetic energy imager. For example, if the temperature of the organisms of the culture is outside of a desired range, perhaps an attendant could reposition the cultures, raise the temperature in the incubator, etc. Certain embodiments of the radiant kinetic energy imager 100 can even include an automated repositioning mechanism to attempt to maintain the temperatures of the organisms at a desired temperature or range of temperatures.

Certain embodiments of the radiant kinetic energy imager 100 can also be used to detect the temperature or radiated kinetic energy of organisms that are contained within humans, animals, etc. Consider that certain embodiments of the radiant kinetic energy imager 100 could be used to analyze or situate organisms such as cancer, viruses, bacteria, etc. that can be located at various portions of the individual (e.g., particularly if situated near the skin, in the breast, etc.), based at least in part on the radiated kinetic energy of the organism. In certain instances, it may be possible to even detect the presence or absence of organisms such as viruses, tumors, bacteria, etc. using certain embodiments of the radiant kinetic energy imager 100, particularly if the temperature of the organism differs considerably from the temperature of the host. Certain embodiments of taking the temperature of the organism can be performed in vivo for the host, and may provide a relatively cost effective mechanism and/or relatively low-invasiveness technique to analyze or provide temperature related information relating to the organism and/or the host.

As such, certain embodiments of the radiant kinetic energy imager 100 can thereby allow for individuals 104 (humans, animals, or organisms) to have their temperature taken with considerably less invasiveness, time, and difficulty than conventional thermometers. In addition, the amount of time and effort to take a reliable temperature by doctors, veterinarians, health care providers, etc. can in certain instances thereby be reduced using a variety of embodiments of the radiant kinetic energy imager 100 as described in this disclosure.

Certain embodiments of the radiant kinetic energy imagers 100 can thereby monitor the entire body, or portions thereof (including, e.g., the front, back, a leg, etc.) to consider the temperature, or regional variations thereof. Certain embodiments of the radiant kinetic energy imagers 100 may not have to contact the individual. Certain embodiments of the radiant kinetic energy imagers 100 can monitor over time, such as continually or over some interval at night, during an operation, during exercise, etc. Certain embodiments of the radiant kinetic energy imagers 100 can interact with temperature and gain information, and thereby utilize the technology to limit interaction or contact with the individual that may be especially desirable when the individual is asleep, or under medication. Certain embodiments of the radiant kinetic energy imagers 100 can detect the individual, if brain dead for example, and could observe more information or a thermal map which may relate to the condition and temperature of the individual. Certain embodiments of the radiant kinetic energy imagers 100 can be integrated with an angiogram or blood test in brain (which may be included as one embodiment of the individual treating portion 94 as described with respect to FIG. 4), such as to sense the individual's condition such as to determine brain death. Certain embodiments of the radiant kinetic energy imagers 100 can closely monitor and/or treat temperature functions of the individual, which may be especially important if, for example, the reason why the individual is being treated (e.g., in the hospital, clinic, or other location) is because of circulatory or vascular problems. With certain embodiments of the radiant kinetic energy imagers 100, the condition of the individual can be monitored, maintained, and/or treated.

Certain embodiments of the radiant kinetic energy imager 100 that can image the radiated kinetic energy may provide improved information about body temperature, sickness, circulatory flow, etc. as compared to certain conventional thermometers. Consider, for example, that the temperature of certain individuals 104 can change over time by up to a few degrees, such as when the individual 104 is resting, unconscious, or sleeping. Taking the temperature of such individuals as patients in hospitals or nursing homes typically requires that the individual 104 wake up. Consider that in certain instances, waking the individual can cause the temperature of the individual to change (e.g., from the resting to awake state) thereby possibly altering the reliability or usability of the derived information. Certain regions of the individual, particularly near the extremities, may be relatively low due when the individual 104 is resting due to reduced blood flow within the individual, etc. Certain embodiments of the radiant kinetic energy imager 100 can provide a variety of temperature information about the individual, either when in the resting or awake state, much of which could relate to circulatory issues. Taking the individual's 104 temperature, such as with the conventional thermometers, typically provides little circulatory information.

Figure 4:
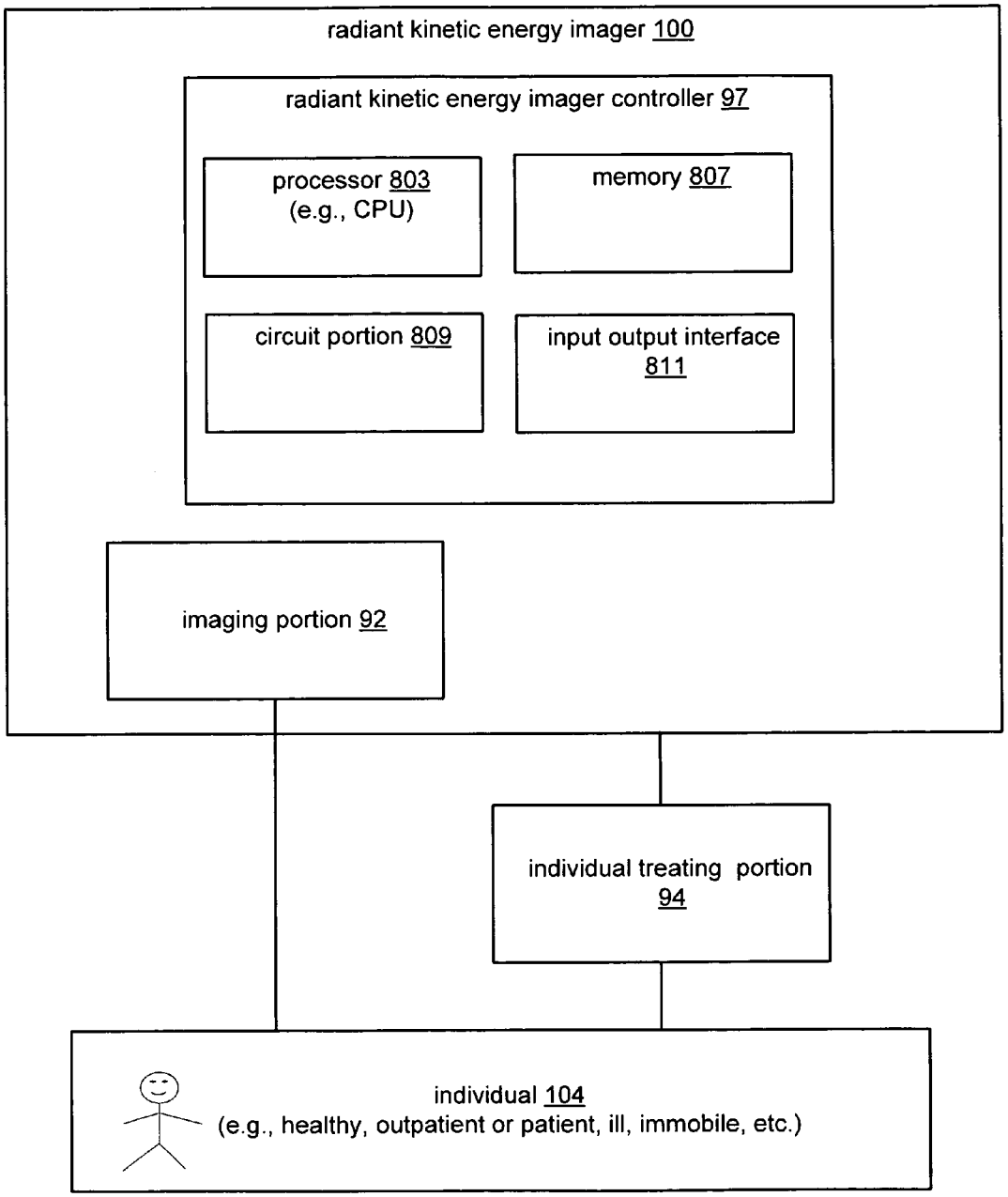
FIG. 4 is a block diagram of an embodiment of the radiant kinetic energy imager.

Certain embodiments of the radiant kinetic energy imager 100 that can interface with the individual 104, as described with respect to FIG. 4 that, as a block diagram, can include, but are not limited to: a radiant kinetic energy imager controller 97, an imaging portion 92, and an individual treating portion 94. Certain embodiments of the radiant kinetic energy imager 100 can, depending upon context as described in this disclosure, image a radiated kinetic energy of the individual. Certain embodiments of the radiant kinetic energy imager controller 97 are described later in this disclosure.

Certain embodiments of conventional thermographic techniques, for example, have been recognized as a digital infrared imaging technique based on the principle that metabolic activity and vascular circulation in both pre-cancerous tissue and the area surrounding a developing breast cancer is almost always higher than in normal breast tissue. Consider, for example, the article contained at the web page http://www-.breastthermography.com/breast_thermography_mf.htm, incorporated by reference in its entirety.

Certain embodiments of the imaging portion 92 can include, but are not limited to, imagers, cameras, digital imaging devices, semiconductor devices, motes, controllers, computer-devices, and other such devices that can image the radiant kinetic energy emitted by the individual 104, such as may be used to detect the radiated kinetic energy.

Certain embodiments of the individual treating portion 94 can be used to position, alert, medicate, or otherwise treat the individual. For example, certain embodiments of the individual treating portion may indicate the individual themselves that they may have reduced circulation, and to recommend that they position themselves accordingly. By comparison, certain embodiments of the individual treating portion 94 can be automated, such as to shift or otherwise position the individual to a desirable location. Certain embodiments of the individual treating portion may act substantially immediately, while other embodiments of the individual treating portion may have some delay for treatment. For example, certain embodiments of the radiant kinetic energy imager 100 can be configured, or programmed, to notify a caretaker of the individual such as the nurses station some duration after temperature in the extremities or other location drops to a certain level; to do so if the temperature doesn't subsequently rise later; or to do so if some other event does not occur in the intervening time period, such that after the time period, the individual may be repositioned or notified to reposition themselves. As such, considerably more information may be made available to a centralized doctor's or nurse's station, as compared to the individual's room. Consider, for example, that the condition, position, temperature map, etc. of an individual patient could be remotely accessed or analyzed, and the condition of the individual could be determined. In those instances, for example, of a patient who repeatedly signals the nurse, for example, the condition of the individual could be closely monitored.

Figure 5:
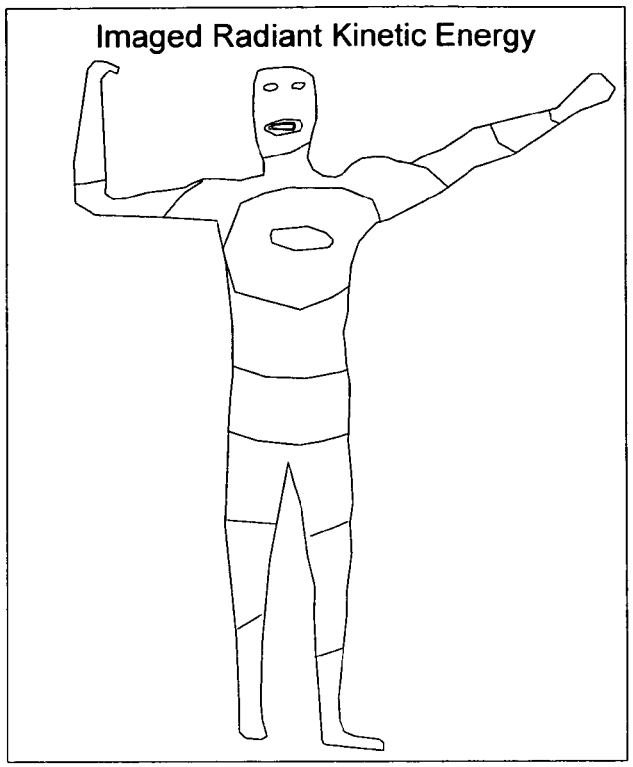
FIG. 5 is a diagram of one embodiment of a radiated kinetic energy such as may be taken by certain radiant kinetic energy imagers as described with respect to FIGS. 1 to 4.
Figure 6:
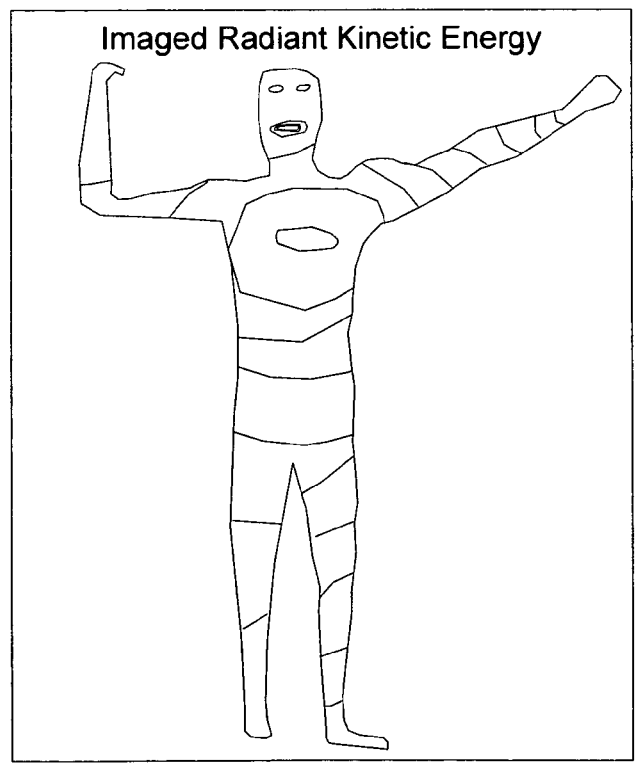
FIG. 6 is a diagram of yet another embodiment of a radiated kinetic energy such as may be taken by certain radiant kinetic energy imagers as described with respect to FIGS. 1 to 4.

Certain embodiments of the radiant kinetic energy imager 100 can, depending upon context, image the radiated kinetic energy, as described with respect to FIGS. 5 and 6. The radiant energy gradient of FIG. 5, for example, is intended to be illustrative and somewhat arbitrary, and the temperature gradient lines may represent a degree, or some fraction of a degree, across the body of the individual 104. FIGS. 5 and 6 provide one example of the radiated kinetic energy which may result from, for example, infrared imaging. Other embodiments, mechanisms, and/or technologies of the radiant kinetic energy imager 100 can be utilized to derive the radiated kinetic energy. A treating physician, veterinarian, etc. may consider such information as the individual 104 sleeping that can be used to explain variations of temperatures within the radiated kinetic energy from some desired value. It is likely, that there are going to be variations in temperature from the ideal or desired temperature. The radiated kinetic energy of FIG. 5, for example, may indicate relatively good circulation in the extremities of the individual 104. In certain instances, for example depending upon context, the extremities of the individual 104 may be a lower temperature than the core temperature of the individual.

Such a difference in temperature can also indicate a true variation that may result from a fever, heat exhaustion, thermal cooling, etc. FIG. 6 illustrates one embodiment of a radiated kinetic energy that may indicate, for example, that one side of the individual 104 (e.g., the right side as shown in FIG. 6) has reduced circulation as compared to the left side, as could be indicated by a decreased spacing (or increased concentration) of the temperature gradient lines. Such reduced circulation may be detected, for example, by relatively sharp temperature reduction in a relatively short distance of the temperature of the individual 104, as may be indicated by relatively closely-situated gradient lines. For example, the temperature taken on lower arms and/or fingers (which are more extremely situated) may be considerably cooler than the upper arm (that are less extremely situated). Under these circumstances, as a result of relatively reduced circulation in the lower arm, it would be desirable to position the arm or other portion of the individual 104, and thereby limit reduced circulation to that part of the body and resultant problems which may be associated therewith. Certain embodiments of the radiant kinetic energy imager 100 indicating, for example, a relatively sharp variation of temperatures across a portion of the body may indicate, for example, relatively reduced circulation in that portion of the body.

Each individual 104, such as a person or animal, thereby can radiate the radiated kinetic energy that can be detected by certain embodiments of the radiant kinetic energy imager 100. Certain embodiments of the radiated kinetic energy can thereby indicate the amount of kinetic energy being radiated from that individual 104 from at least one location across the body of the individual. Certain embodiments of the radiant energy signature may thereby provide a more thorough analysis of the condition of the individual 104. In numerous instances, it is therefore likely as illustrated in FIGS. 5 and 6 that the individual's kinetic energy signature may not be uniform across the entire individual, and instead may be characterized as gradient (and such gradients may be indicative of reduced circulation, inactivity, injury, etc.). For example, certain areas of the individual 104 traditionally receive less blood flow than others, and thereby may appear cooler than others during, at least in part, imaging techniques. In general, the areas of the individual's 104 body which obtained less blood flow, and thereby may appear to generate less radiant kinetic energy, are thereby those areas which will likely have reduced circulation. In addition, those areas of the body which have less circulation may be more likely to "fall asleep", or have circulatory problems such as may result in gangrene, etc. than other areas of the individual's 104 body, etc.

There may be a number of reasons why determining areas of altered circulation, such as can be detected by certain embodiments of the radiant kinetic energy imager 100, may be desirable. One reason to determine an area of reduced circulation in the individual 104 can include, but is not limited to: reducing the occurrence of bed sores for bedridden, wheelchair, or handicapped individuals 104. Another reason to determine an area of reduced circulation in the individual 104 may be to improve the blood circulation for travelers, those sitting in chairs for long times, etc. In general, those times that the individual may be exposed to reduced circulation may be considered as a warning or a concern, and therefore certain embodiments of the radiant genetic energy imager 100 may be utilized.

Certain embodiments of the radiant kinetic energy imager 100 can thereby be used to determine the absolute and/or relative temperature at a number of locations across the individual 104. For example, it may be desirable to determine a temperature of the individual 104 in a hospital, nursing home, doctors office, etc., as described with respect to FIGS. 1 to 3 without having to use a thermometer. It is envisioned that in a doctors office, for example, certain embodiments of the radiant kinetic energy imager 100 could determine the individual's 104 temperature as they wait or walk in a waiting room, hallway, room, etc. as described with respect to FIG. 2. Additionally, it may not be necessary that a person such as a physician, medical technician, etc. may be registered to take the temperature of the individual 104. Additionally, even taking a temperature for an individual 104 can be a time-consuming operation, and certain embodiments of the radiant kinetic energy imager 100 can provide a mechanism to take a temperature.

While certain embodiments of the radiant kinetic energy imager 100 can provide a variety of temperature-related information, it is envisioned that such information may be used in combination, with instead of, or in addition to the conventional thermometers. As such, conventional thermometers and/or thermometer equipment are envisioned to be used in a variety of situations, and by a number of medical practitioners. It is envisioned that the thermal map/signature information that can be provided about the individuals can be utilized to provide a variety of information about the individual's health, condition, temperature, etc.

Certain embodiments of the radiant kinetic energy imager 100 can be used to determine whether the temperature indicated should be relied upon, or whether there might be some reason to justify an inaccurate temperature. For example, the individual 104 having a body core temperature that is generally close to a "normal" temperature, but having a portion of that is different from normal but should be normal, may be at least partially explained by an additional source indicating the individual 104 is wearing clothing, etc. over that region, or has some kinetic energy-generating equipment such as a radio or cellular telephone close to that region. A variety of embodiments of the additional source can be considered that may include, but is not limited to: a human visually observing the individual 104, a camera, detector, imager, controller, computer-device, mote device, etc. which may or may not be included in the radiant kinetic energy imager 100 detecting what the individual 104 is wearing, using, or is proximate the individual, etc. A variety of embodiments of detection logic (not illustrated) may be included which may indicate to certain embodiments of the radiant kinetic energy imager 100 why an apparent erroneous temperature indication exists for at least a portion of the individual 104. Certain embodiments of the radiant kinetic energy imager 100 can be configured to operate through relatively light clothing, but may not operate through heavy clothing such as heavy coats. As such, certain operators of certain embodiments of the radiant kinetic energy imager 100 should be aware of the clothing of the individual to ensure proper operation.

A number of embodiments of the radiant kinetic energy imager 100 may be provided may be situated, for example but not limited to, as a standalone device in a hall, room, outside, scanning region, etc. A variety of technologies may also be utilized in certain embodiments of the radiant kinetic energy imager 100 that may include, but not limited to, semiconductor imaging devices, optical imaging devices, photographic devices, computer devices, telephonic devices, controller devices, etc. Certain embodiments of the radiant kinetic energy imager 100 may even be situated, for example, within the individual's 104 bed, seat, couch, etc. such as to be able to ascertain the individual's temperature from close proximity. Certain ones of these embedded embodiments of the radiant kinetic energy imager can include discrete temperature devices embedded across different locations of the furniture or bed, a planar-detector situated near the surface of the furniture, etc. Certain embodiments of the radiant kinetic energy imager 100 can even utilize positioning technology (not illustrated), which can determine the approximate positioning of the individual 104 based upon either temperatures of various locations, or alternatively pressure sensors, contact sensors, etc.

In certain instances, the individual 104 may not even be aware of their reduced circulation until such time as they move that portion of their body. For example, a person sitting in a movie theater, watching TV, etc. may not even be aware that a bodily part of theirs is falling asleep until, perhaps, they move. These aspects are true both for individuals in hospitals, nursing homes, and other clinical applications as well as individuals in non-clinical and/or non-medical applications. Certain embodiments of the radiant kinetic energy imager 100 can even indicate to the individual 104 of a relatively reduced circulation condition, and certain embodiments may even recommend the individual move themselves, or alternatively provide a mechanism to move the individual 104, or indicate to another to move the individual to improve circulation as described in this disclosure.

Since there are a variety of temperatures of the radiation that the radiant kinetic energy imager 100 is imaging (across the body, etc.), certain embodiments of the radiant kinetic energy imager 100 can perform a variety of techniques and/or use a variety of mechanisms to indicate a representative temperature of the individual 104. In certain home, office, hospital, or other settings, the temperature of a room or area in which the individual is situated could be adjusted based on the derived temperature(s) of the individual 104.

Certain embodiments of the radiant kinetic energy imager 100 can correlate the received radiation from some location that temperatures are typically taken using a variety of conventional thermometers (within or around the mouth, under the arms, etc.). The various correlated readings at the suitable location on the individual 104 can indicate the temperature at the desired location of the individual 104. For example, certain embodiments of the radiant kinetic energy imager 100 can utilize infrared imaging to determine the kinetic energy generated at the mouth, under the arm, etc.; and each color can be correlated to a particular temperature as could be detected using a computer or manually. Infrared imaging, for example, may be used to detect such temperatures utilizing imaging technologies even through certain clothing of the individual 104. Other mechanisms, which can sense kinetic energy, for example, may be used to sense a radiated kinetic energy across the individual 104.

Certain embodiments of the radiant kinetic energy imager 100 can determine the temperature of the individual 104 by considering the radiated kinetic energy across the individual 104. For example, one or more kinetic energy gradient images can be taken of the individual 104, and either the corresponding temperature of the particular regions can be taken. Alternately, the radiated kinetic energy across the individual 104 can be considered, and the radiated kinetic energy can be searched for "relatively" cool or cold spots utilizing either visual, computerized, or digital image processing techniques, etc. Such cool spots may be indicative of the reduced circulation at least at the respective cool spot of the individual 104. Certain embodiments of the radiant kinetic energy imager 100 can thereby position the individual 104 (either immediately or after some delay) based at least in part on sensing the cool spots or cold spots, as described in this disclosure.

Certain embodiments of the radiant kinetic energy imager 100 can thereby image a temperature of such individuals 104 as resting or sleeping persons (e.g., in the middle of the night). As such, certain embodiments of the radiant kinetic energy imager 100 can provide an indication of the temperature of the individual 104, even without waking the individual. Consider the number of patients in hospitals or nursing homes who have to be awaken to have their temperature taken using conventional thermometers, in certain instances to ensure the condition of the individual. Certain embodiments of the radiant kinetic energy imager 100 can, in general, detect changes or trends in temperature, such as to obviate the necessity to awake the individual 104 to take the temperature of the individual. Other individuals, such as humans or animals, may utilize the radiant kinetic energy imager 100 to monitor temperature without having to wake up the individual. In such a manner, the health-care provider can also gain valuable information about the individual 104 to ensure that the individual is not suffering from a large temperature variation such as may be indicative of reduced circulation, shock, injury, or even impending death even during sleep or rest.

As such even under those circumstances that the individual 104 is unconscious, asleep, seriously injured or ill, or otherwise incommunicative, certain embodiments of the radiant kinetic energy imager 100 can even detect (perhaps even for the individual 104) reduced circulatory regions. In instances where the individual normally has poor circulation, certain embodiments of the radiant kinetic energy imager 100 can monitor the circulation (or body temperature(s)) of the individual against dropping to a dangerously low level.

Figure 7A:
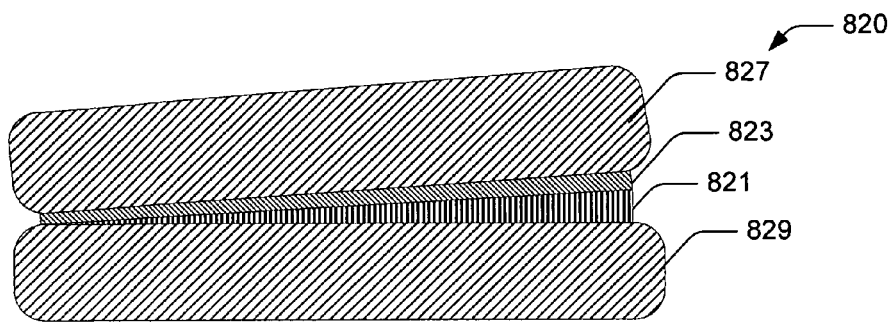
FIGS. 7a and 7b, is a diagram of one embodiment of a positioning mechanism.
Figure 7B:
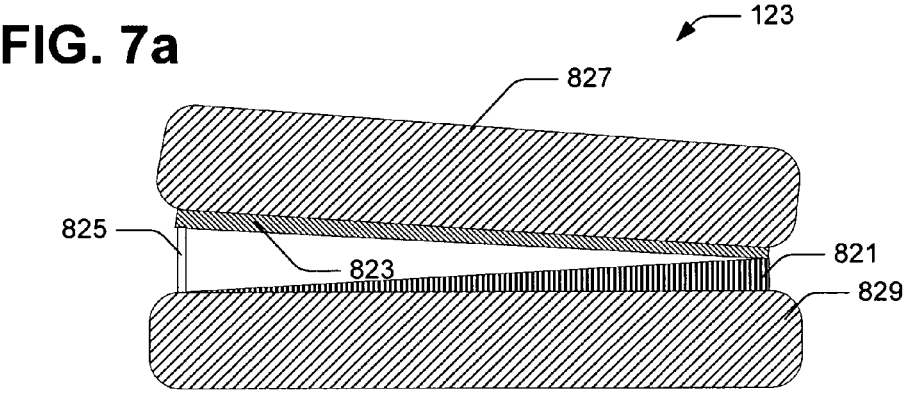

Certain embodiments of the radiant kinetic energy imager 100 can include a variety of embodiments of the positioning mechanism 100 which can be configured to position the individual 104. For example, as illustrated in FIG. 7 (which includes FIGS. 7a and 7b), for example, a positioning mechanism 123 can be provided that could, for example, shift a position of the individual 104. The embodiment of the positioning mechanism 123 as described with respect to FIGS. 7a and 7b is intended to be relatively simplified, including an incline plane 821, an individual positioning portion 823, and an actuating mechanism 825, as well as an upper mattress 827 and a lower mattress 829. Certain embodiments of the radiant kinetic energy imager 100 and/or positioning mechanism 123 can be utilized in a variety of bed, couch, operating table, or other configurations. The individual positioning portion 823, for example, when actuated by the actuating mechanism can act to shift a considerable amount of the weight of the individual from one side of the individual to another side of the individual, when the individual is resting on the positioning mechanism. Certain embodiments of the positioning mechanism can be actuated, for example, when certain embodiments of the radiant kinetic energy imager senses a physiologically-indicating body temperature of the individual, such as the individual likely being able to form bed sores, etc.

Other similar embodiments of the positioning mechanism 123, for example, can be provided in beds, chairs, vehicles, couches, or other locations that such individuals as humans, or even animals, are likely to sit or rest for an extended period, or alternately be located in an unconscious, asleep, medicated, or other state that they are unlikely to move. For example, those individuals 104 that may be unable to move, such as one in a coma, under anesthesia, a paraplegic, a quadriplegic, etc. may be shifted from one position to another (e.g., the body weight being shifted from one side to another). Such shifting a body weight, based at least in part upon sensed circulatory conditions, may have the tendency to reduce bed sores, etc. Within hospitals, nursing homes, and other locations of seriously injured, unconscious, bedridden individuals, etc., the process of detecting and/or treating bed sores is a serious health consideration.

Certain embodiments of the positioning mechanism can be configured, instead of positioning the individual themselves, can instead notify the individual, an attendant, or assistant, to shift the individual. Consider a number of medical technician's, attendants', or nurses' backs have been injured by attempting to lift, shift, or shift conscious or unconscious people. As such, certain embodiments of the positioning mechanism 123 as described with respect to FIGS. 7a and 7b can be beneficial to others than the individual who may attempt to shift the individual, as well.

Certain embodiments of the positioning mechanism 123 can thereby be automated, such as to shift the position of the individual 104 upon a sensed condition such as reduced circulation as indicated by certain embodiments of the radiant kinetic energy imager 100. By comparison, certain embodiments of the positioning mechanism 123 can be mechanical, such as a mechanical weight-shifting device that can be actuated by a health-care provider, a family member, a friend, etc. can shift the individual 104 upon the appropriate sensed condition provided by certain embodiments of the radiant kinetic energy imager 100. Alternatively, certain embodiments of the positioning mechanism 123 can at least partially include the health-care provider, family member, friend, etc. who upon suitable indication by the radiant kinetic energy imager 100, can manually "shove" the individual 104 to a suitable position.

Certain embodiments of the positioning mechanism 123 can operate quickly, or there may be a delay in certain embodiments of the positioning mechanism. For example, certain embodiments of the radiant kinetic energy imager 100 can detect a state of the radiated kinetic energy that may indicate reduced circulation, and thereupon actuate the positioning mechanism 123 seconds, minutes, or even after the sensed state indicted by the radiated kinetic energy.

Certain embodiments of the radiant kinetic energy imager 100 could also at least partially sense noise, aromas, physiologic signals, etc. (alternative to or in addition to the radiated kinetic energy) to sense reduced circulation, temperature etc. Certain embodiments of the radiant kinetic energy imager 100 may also include not only effecting a change, but alerting a change agent to position the individual 104 (e.g., where a variation of application one way or another doesn't matter). Certain embodiments of the radiant kinetic energy imager 100 can even be associated with a treating portion (such as to apply medication), such that the output of the radiant kinetic energy imager 100 can apply a medication schedule or health regimen schedule. Certain embodiments of the bed, seat, couch, ground surface, floor, etc. where the individual 104 is situated may have embedded radiant kinetic energy imagers that can act as at least portions of the radiant kinetic energy imager 100 which may depend on its particular application.

Certain embodiments of the radiant kinetic energy imager 100 can transmit, network, or otherwise transfer images, data, text, or other information to another location such as can be used to monitor the individual. Consider, for example, the embodiment of the individual display 920 that can be configured to include a centralized location that can switch between monitoring radiant kinetic energy obtained from a number of disseminated radiant kinetic energy imagers 100 with the information being displayed, as described with respect to FIG. 9. Certain embodiments of the individual display 920 that are being used to monitor patients, for example, can display information about the individual to a nurse station, a doctor's office, etc. Within this disclosure, the term "display" can, depending upon context, include any mechanism that can provide information to another person such as a physician, etc. such as a display, a graphical user interface (GUI), an audio device, a speaker, a text-presenter, etc.

Certain embodiments of the individual display 920 can thereby be configured to provide sufficient information to a physician, medical assistant, nurse, etc. to monitor a variety of aspects relating to the individual that can include, but is not limited to, radiant kinetic energy as emitted from the individual. Certain multi-individual treating facilities (such as hospitals, nursing homes, etc.) can utilize networking, switching, computer, communication, controller, monitoring, and other associated technologies such as would be known to one skilled in the networking and computer technologies to allow the individuals to be monitored remotely utilizing suitable technology. For example, as described with respect to FIG. 9, vital statistics of each patient can be monitored by certain embodiments of the individual display 920, such as may include, but is not necessarily limited to, heart rate, blood pressure, EKG, ECG, etc. Certain embodiments of the individual display 920 can provide such information to the physician or other medical personnel as a thermal map including the radiant kinetic energy radiated from the individual. Such radiant kinetic energy information as may be provided by the thermal map and/or individual display 920 can be utilized to indicate that the individual should be re-positioned or reposition themselves to be treated, etc., which can be done either by providing a display or other prompt to the individual, notify the medical personnel to position the individual, or trigger some automated mechanism such as described with respect to FIGS. 7a and 7b to reposition the individual. In addition, certain embodiments of the radiant kinetic energy information as displayed on the individual display 920 of FIG. 9 can indicate a suitable condition and location on the individual for bed sores, ulcers, the occurrence of a septic condition, or other infections, etc.

By utilizing certain embodiments of the radiant kinetic energy information as displayed on the individual display 920, certain physicians or other medical personnel can obtain a variety of important information such as may be useful for treating the individual, even from a remote location such as a doctor's office or home. Certain embodiments can even provide for home medical care in which the monitoring and/or treatment may be comparable to that in a hospital or nursing home, etc. For example, a relatively complete map of the individual can be provided to the doctor or medical assistant. In addition, the position of the individual (based at least in part on the imaged radiant kinetic energy) which can be real-time of other, can be determined. Also, the amount the individual is moving can be monitored to determine, for example, how well the individual is resting, the comfort of the individual, as well as the health or condition of the individual.

Certain embodiments of the radiant kinetic energy information as displayed on the individual display 920, such as described with respect to FIGS. 9 and 10, can even indicate an injury, illness, or condition such as being septic. For example, if the periphery of the individual is warm as compared to the interior (core) temperature, the individual may be septic. As such, certain embodiments of the radiant kinetic energy imager 100 can be configured to improve detection of, as well as monitor, certain temperature-based illnesses, injuries, or conditions such as may be useful in improving health care.

Figure 11:
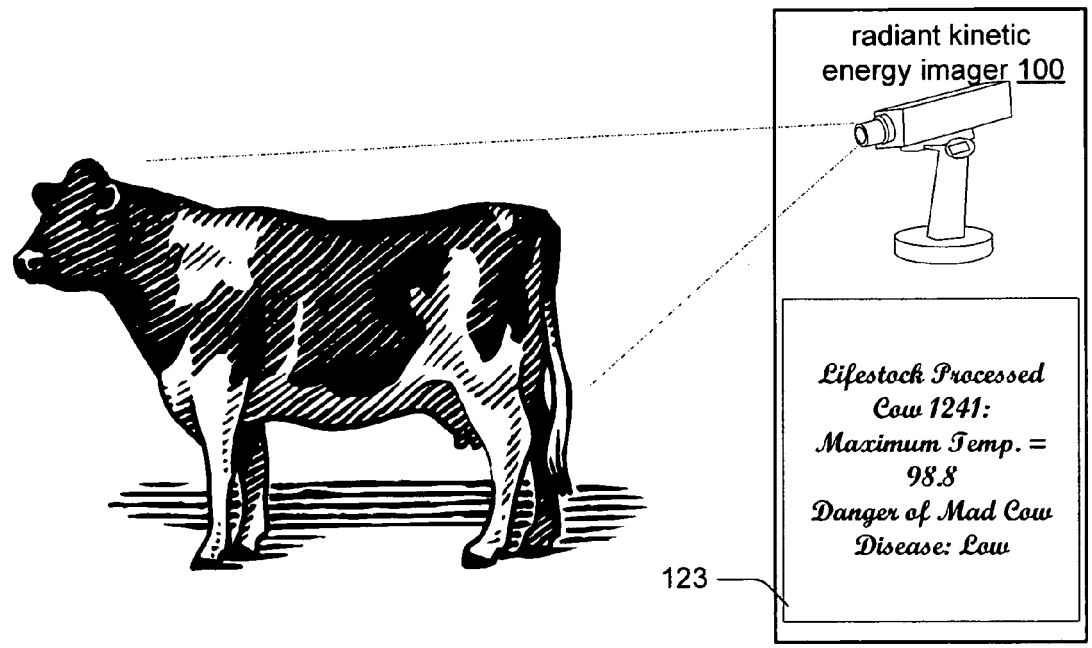
FIG. 11 is a diagram of another embodiment of a radiant kinetic energy imager as can be applied to another individual who is a livestock animal.

Certain embodiments of the radiant kinetic energy imager 100, as described with respect to FIG. 11, can be configured to sense illnesses, injuries, and/or conditions of livestock. To take the temperature of each cow, horse, or other livestock "individual", for example, can be quite time consuming using certain embodiments of traditional animal thermometers and can be otherwise undesirable. It would be desirable to screen multiple cows being sold, for example, using certain embodiments of the radiant kinetic energy imager 100. Certain embodiments of the radiant kinetic energy imager 100 can thereby be used to limit the sale or transfer of sick animals, and the associated contamination of other animals. Certain embodiments of the radiant kinetic energy imager 100 could, for example, be utilized in and/or directed at walkways or corrals where the animals may be expected to be traversing. Other embodiments of the radiant kinetic energy imager 100 could, for example, also be directed at animals in fields, cages, crates, etc. wherein the temperature of the animals could be determined using imaging techniques without the necessity of further interfacing with the animal and/or perhaps moving the animal to another location. Certain embodiments of the radiant kinetic energy imager 100 could thereby be utilized to monitor the temperature, and perhaps health, of livestock and certain other animals.

2. Certain Embodiments of the Radiant Kinetic Energy Imager Controller

This disclosure describes a number of embodiments of the radiant kinetic energy imager controller 97 as described with respect to FIG. 4, which are intended to control operations of the radiant kinetic energy imager 100. Certain embodiments of the radiant kinetic energy imager 100 can include the radiant kinetic energy imager controller 97 to control at least some of its operations; while other embodiments of the radiant kinetic energy imager may not include utilizing certain embodiments of the radiant kinetic energy imager controller. For instance, certain embodiments of the radiant kinetic energy imager 100 can include the radiant kinetic energy imager controller 97, which can be largely microprocessor-based, and can provide for largely automated operation or assembly of the radiant kinetic energy imager 100. By comparison, certain embodiments of the radiant kinetic energy imager 100 can be operated utilizing largely manual techniques, and may not utilize the radiant kinetic energy imager controller 97. FIG. 4 thereby shows a block diagram of certain embodiments of the radiant kinetic energy imager 100 that can include the radiant kinetic energy imager controller 97.

Certain embodiments of the radiant kinetic energy imager 100 thereby can include, but may not be limited to, any particular configuration of the radiant kinetic energy imager controller 97. Certain embodiments of the radiant kinetic energy imager controller 97 can be computer based, controller based, mote based, cellular telephone-based, and/or electronics based. Certain embodiments of the radiant kinetic energy imager controller can be segmented into modules or network nodes, and can utilize a variety of wireless communications and/or networking technologies to allow information, data, etc. to be transferred to the various distinct portions or embodiments to perform, a variety of operations associated with the radiant kinetic energy imager 100. Certain embodiments of the radiant kinetic energy imager controller 97 can be configured as a unitary or stand alone device.

Certain embodiments of the radiant kinetic energy imager controller 97 can vary as to their automation, complexity, and/or sophistication; and can be utilized to control, setup, establish, and/or maintain communications between a number of communicating devices. As described within this disclosure, multiple ones of the different embodiments of the radiant kinetic energy imager 100 can transfer information or data relating to the communication link to or from a remote location and/or some intermediate device as might be associated with communication, monitoring and/or other activities.

Certain embodiments of the radiant kinetic energy imager controller 97, as well as certain embodiments of the radiant kinetic energy imager 100 (in general), can utilize distinct firmware, hardware, and/or software technology. For example, mote-based technology, microprocessor-based technology, microcomputer-based technology, general-purpose computer technology, specific-purpose computer technology, Application-Specific Integrated Circuits, and/or a variety of other computer technologies can be utilized for certain embodiments of at least a portion of the radiant kinetic energy imager controller 97, as well as be included in certain embodiments of the radiant kinetic energy imager 100.

Certain embodiments of the radiant kinetic energy imager controller 97 can as described with respect to FIG. 4 can include a processor 803 such as a central processing unit (CPU), a memory 807, a circuit or circuit portion 809, and an input output interface (I/O) 811 that may include a bus (not shown). Certain embodiments of the radiant kinetic energy imager controller 97 of the radiant kinetic energy imager 100 can include and/or be a portion of a general-purpose computer, a specific-purpose computer, a microprocessor, a microcontroller, a personal display assistant (PDA), a cellular phone, a digital phone, a wireless communicating device, a hard-wired phone, and/or any other known suitable type of communications device, computer, and/or controller that can be implemented in hardware, software, electromechanical devices, and/or firmware. Certain embodiments of the processor 803, as described with respect to FIG. 4, can perform the processing and arithmetic operations for certain embodiments of the radiant kinetic energy imager controller 97 of the radiant kinetic energy imager 100. Certain embodiments of the radiant kinetic energy imager controller 97 of the radiant kinetic energy imager 100 can control the signal processing, database querying and response, computational, timing, data transfer, and other processes associated with certain embodiments of the radiant kinetic energy imager controller 97 of the radiant kinetic energy imager 100.

Certain embodiments of the memory 807 of the radiant kinetic energy imager controller 97 can include a random access memory (RAM) and/or read only memory (ROM) that together can store the computer programs, operands, and other parameters that control the operation of certain embodiments of the radiant kinetic energy imager controller 97 of the radiant kinetic energy imager 100. The memory 807 can be configurable to contain information obtained, retained, or captured by that particular radiant kinetic energy imager controller 97 of the radiant kinetic energy imager 100.

Certain embodiments of the bus can be configurable to provide for digital information transmissions between the processor 803, circuits 809, memory 807, I/O 811, and/or the image memory or storage device (which may be integrated or removable). In this disclosure, the memory 807 can be configurable as RAM, flash memory, semiconductor-based memory, of any other type of memory that can be configurable to store data pertaining to images. The bus also connects I/O 811 to the portions of certain embodiments of the radiant kinetic energy imager controller 97 of either the radiant kinetic energy imager 100 that can either receive digital information from, or transmit digital information to other portions of the radiant kinetic energy imager 100, or other systems and/or networking components associated therewith.

Certain embodiments of the radiant kinetic energy imager controller 97 of the radiant kinetic energy imager 100, as described with respect to FIG. 4, can include a transmitter portion (not shown) that can be either included as a portion of certain embodiments of the radiant kinetic energy imager controller 97 of the radiant kinetic energy imager 100. Certain embodiments of the radiant kinetic energy imager controller 97 can alternately be provided as a separate unit (e.g., microprocessor-based). In certain embodiments, the transmitter portion can transmit image information between certain embodiments of the radiant kinetic energy imager controller 97 of the radiant kinetic energy imager 100.

Certain embodiments of the radiant kinetic energy imager controller 97 of the radiant kinetic energy imager 100 as described with respect to FIG. 4 can include an operation altering portion (not shown) that can be either included as a portion of certain embodiments of the radiant kinetic energy imager controller 97 of the radiant kinetic energy imager 100, or alternately can be provided as a separate unit (e.g., microprocessor-based).

Certain embodiments of the memory 807 can provide one example of a memory storage portion. In certain embodiments, the monitored value includes but is not limited to: a percentage of the memory 807, an indication of data that is or can be stored in the memory 807, or for data storage or recording interval. To provide for overflow ability for the memory 807 of certain embodiments of the radiant kinetic energy imager controller 97 of the radiant kinetic energy imager 100, a secondary storage device can be operably coupled to the memory 807 to allow a controllable transmitting of memory data from certain embodiments of the radiant kinetic energy imager controller 97 of the radiant kinetic energy imager 100 when the monitored value of data or other information within the memory 807 exceeds a prescribed value. The prescribed value can include, e.g., some percentage amount or some actual amount of the value.

In certain embodiments, a secondary communication link can be established between the certain embodiments of the radiant kinetic energy imager controller 97 of the radiant kinetic energy imager 100. The secondary communication link can be structured in a similar manner as, or indeed act as, a communication link; or alternatively can utilize network-based computer connections, Internet connections, etc. to provide information and/or data transfer between certain embodiments of the radiant kinetic energy imager controller 97 of the radiant kinetic energy imager 100.

In certain embodiments of the radiant kinetic energy imager controller 97 of the radiant kinetic energy imager 100, the particular elements of certain embodiments of the radiant kinetic energy imager controller 97 of the radiant kinetic energy imager 100 (e.g., the processor 803, the memory 807, the circuits 809, and/or the I/O 811) can provide a monitoring function to convert raw data as displayed by an indicator. A monitoring function as provided by certain embodiments of the radiant kinetic energy imager controller 97 of the radiant kinetic energy imager 100 can be compared to a prescribed limit, such as whether the number of images contained in the memory 807, the amount of data contained within the memory 807, or some other measure relating to the memory is approaching some value. The limits to the value can, in different embodiments, be controlled by the user or the manufacturer of certain embodiments of the radiant kinetic energy imager controller 97 of the radiant kinetic energy imager 100. In certain embodiments, the memory 807 can store but should not be limited to such information as: data, information, displayable information, readable text, motion images, video images, and/or audio images, etc.

In certain embodiments, the I/O 811 provides an interface to control the transmissions of digital information between each of the components in certain embodiments of the radiant kinetic energy imager controller 97 of the radiant kinetic energy imager 100. The I/O 811 also provides an interface between the components of certain embodiments of the radiant kinetic energy imager controller 97 of the radiant kinetic energy imager 100. The circuits 809 can include such other user interface devices as a display and/or a keyboard. In other embodiments, the radiant kinetic energy imager controller 97 of the radiant kinetic energy imager 100 can be constructed as a specific-purpose computer such as an application-specific integrated circuit (ASIC), a microprocessor, a microcomputer, or other similar devices.

As such, various embodiments of the radiant kinetic energy imager 100 and/or the radiant kinetic energy imager controller 97 can be configured utilizing relatively complex or simple computer and/or controller technology. As computer and/or controller technology evolves, it is intended that certain embodiments of the radiant kinetic energy imager 100 and/or the radiant kinetic energy imager controller 97 can be modified or adapted to utilize the modifying technology.

3. Certain Embodiments of Radiant Kinetic Energy Imager and/or Radiant Kinetic Energy Imager Controller with Relevant Flowcharts Within the disclosure, flow charts of the type described in this disclosure apply to method steps as performed by a computer or controller. The flow charts can also apply to one or more apparatus devices, such as an imaging device that can include, e.g., a general-purpose computer or specialized-purpose computer whose structure along with the software, firmware, electromechanical devices, and/or hardware, can perform the process or technique described in the flow chart.

Figure 12:
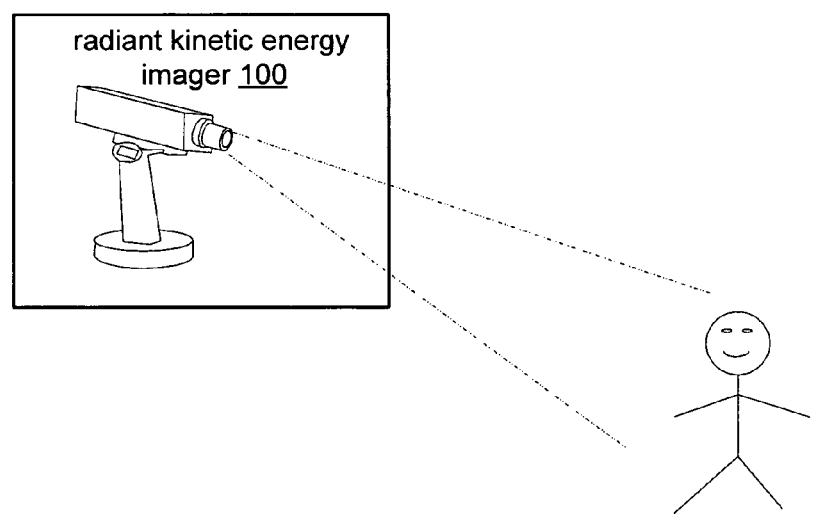
FIG. 12 is a diagram of one embodiment of a display configured as a positioning mechanism indicating, among other things, radiated kinetic energy from the individual.

FIG. 12 shows one embodiment of the radiant kinetic energy imager 100 that can be configured to adjust a positional state of the individual 104 to a physiological aspect of the individual at least partially in response to detecting a radiant kinetic energy from the individual. There can be a variety of embodiments of the radiant kinetic energy imager 100 of FIG. 12 that can be configured, and or operate, similar to as described in this disclosure with respect to FIGS. 1 to 11, for example.

Figure 13A:
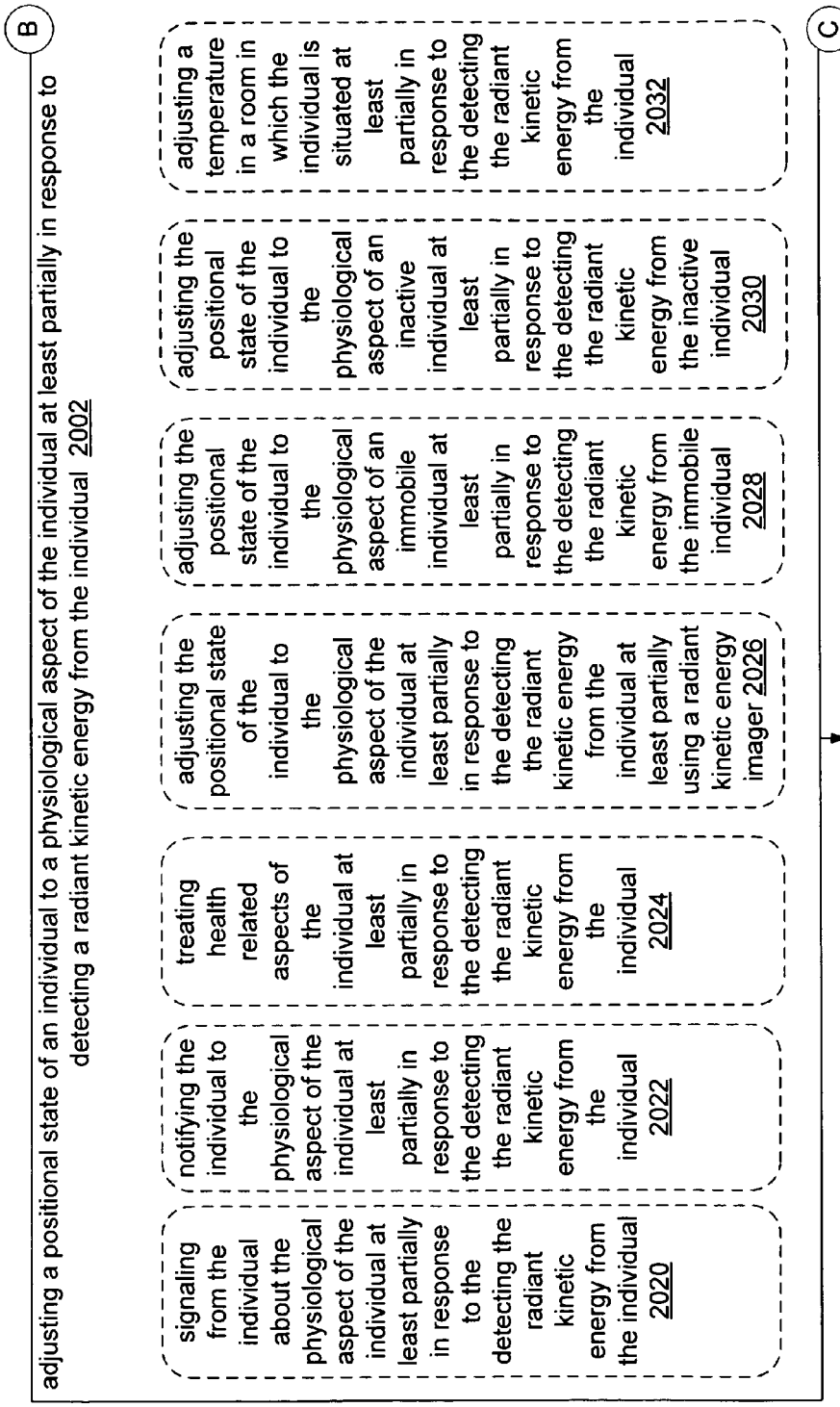
FIGS. 13a and 13b, is a diagram of two embodiments of sample radiated outputs from individuals, such as may be included in the display as described with respect to FIG. 12.
Figure 13B:
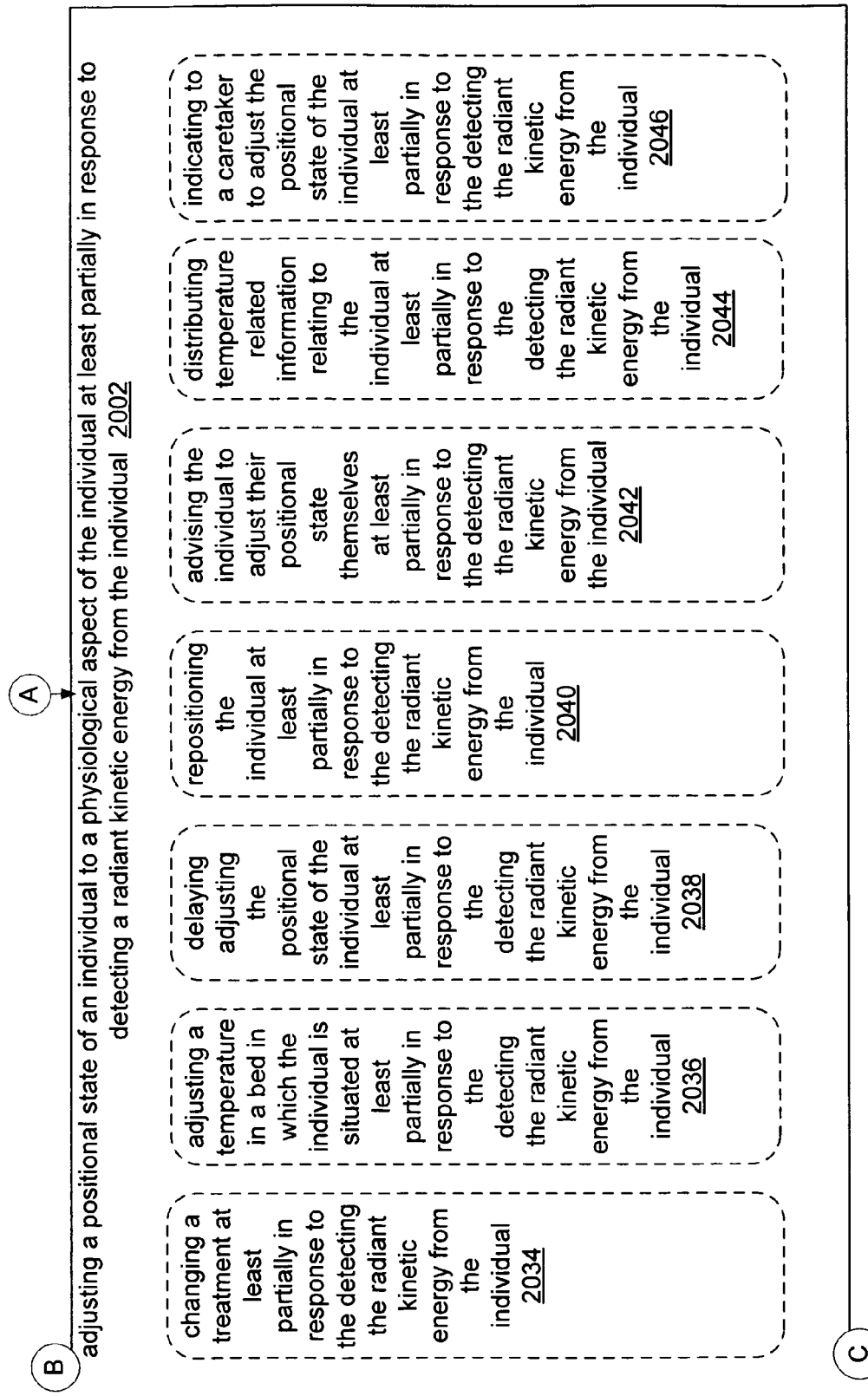

One embodiment of a high-level flowchart of a radiant kinetic energy sensing technique 2000 is described with respect to FIG. 13 (including FIGS. 13*a* and 13*b*) and can include, but is not limited to, operation 2002. One embodiment of operation 2002 can include, but is not limited to, operations 2020, 2022, 2024, 2026, 2028, 2030, 2032, 2034, 2036, 2038, 2040, 2042, 2044, and/or 2046. The high-level flowchart of FIG. 13 (including FIGS. 13*a* and 13*b*) should be considered in combination with the embodiments of the radiant kinetic energy imager 100, as described with respect to FIG. 12. One embodiment of operation 2002 can include, but is not limited to, adjusting a positional state of an individual to a physiological aspect of the individual at least partially in response to detecting a radiant kinetic energy from the individual. For example, the individual can be positioned or repositioned based, at least in part, on certain physiological aspects such as poor circulation, injuries, sicknesses, tumors, etc. of the individual. The individual can be monitored at least partially in response to detecting a radiant kinetic energy from an individual, such as by using the at least one radiant kinetic energy imager 100 as described in this disclosure. One embodiment of the adjusting a positional state of an individual to a physiological aspect of the individual at least partially in response to detecting a radiant kinetic energy from the individual of operation 2002 can include operation 2020, that can include but is not limited to, signaling from the individual about the physiological aspect of the individual at least partially in response to the detecting the radiant kinetic energy from the individual. For example, transmitting information relating to the physiological aspect of the individual (using computer, networking, controller, imaging, or other similar technologies), such as might have been derived from the detected kinetic energy of the individual. Certain embodiments of the adjusting a positional state of an individual to a physiological aspect of the individual at least partially in response to detecting a radiant kinetic energy from the individual of operation 2002 can include operation 2022, that can include but is not limited to, notifying the individual to the physiological aspect of the individual at least partially in response to the detecting the radiant kinetic energy from the individual. For example, notifying the physiological aspect of the individual (using computer, networking, controller, imaging, or other similar technologies), such as might have been derived from the detected kinetic energy of the individual. One embodiment of the adjusting a positional state of an individual to a physiological aspect of the individual at least partially in response to detecting a radiant kinetic energy from the individual of operation 2002 can include operation 2024, that can include but is not limited to, treating health related aspects of the individual at least partially in response to the detecting the radiant kinetic energy from the individual. For example, treating health-related aspects of the individual (e.g., circulatory aspects, lack of $O_2$ aspects, blood pressure aspects, etc.) at least partially in response to detecting the radiant kinetic energy from the individual. One embodiment of the adjusting a positional state of an individual to a physiological aspect of the individual at least partially in response to detecting a radiant kinetic energy from the individual of operation 2002 can include operation 2026, that can include but is not limited to, adjusting the positional state of the individual to the physiological aspect of the individual at least partially in response to the detecting the radiant kinetic energy from the individual at least partially using a radiant kinetic energy imager. For example, certain embodiments of a radiant kinetic energy imager (such as a camera, imaging device, infrared imaging device, etc.) can monitor the physiological aspects of the individual. One embodiment of the adjusting a positional state of an individual to a physiological aspect of the individual at least partially in response to detecting a radiant kinetic energy from the individual of operation 2002 can include operation 2028, that can include but is not limited to, adjusting the positional state of the individual to the physiological aspect of an immobile individual at least partially in response to the detecting the radiant kinetic energy from the immobile individual. For example, certain embodiments of the individual who is being monitored can be immobile, such as, but not limited to, an intensive care patient, paraplegic or quadriplegic patients, a surgical patient, an individual under generalized or local anesthesia, certain rest-home patients, certain in-home carte patients, etc. One embodiment of the adjusting a positional state of an individual to a physiological aspect of the individual at least partially in response to detecting a radiant kinetic energy from the individual of operation 2002 can include operation 2030, that can include but is not limited to, adjusting the positional state of the individual to the physiological aspect of an inactive individual at least partially in response to the detecting the radiant kinetic energy from the inactive individual. For example, monitoring the physiological aspect of an individual who is reclining, sitting, sleeping, flying, at work, etc. One embodiment of the adjusting a positional state of an individual to a physiological aspect of the individual at least partially in response to detecting a radiant kinetic energy from the individual of operation 2002 can include operation 2032, that can include but is not limited to, adjusting a temperature in a room in which the individual is situated at least partially in response to the detecting the radiant kinetic energy from the individual. For example, adjusting a temperature of the environment of the individual (e.g., of a bed, sofa, room, portion thereof, or space), at which the individual is situated. Within this disclosure, adjusting, actuating, or any other suitable action relating to certain embodiments of the radiant kinetic energy imager 100 could be delayed in time following the detecting. For example, certain embodiments of the radiant kinetic energy imager 100 can be configured, or programmed, to notify a caretaker of the individual such as the nurses station some duration after temperature in the extremities or other location drops to a certain level; to do so if it the temperature doesn't subsequently rise later; or to do so if some other event does not occur in the intervening time period. One embodiment of the adjusting a positional state of an individual to a physiological aspect of the individual at least partially in response to detecting a radiant kinetic energy from the individual of operation 2002 can include operation 2034, that can include but is not limited to, changing a treatment at least partially in response to the detecting the radiant kinetic energy from the individual. For example, the individual can be medicated or otherwise treated at least partially in response to the radiant kinetic energy detected from the individual. One embodiment of the adjusting a positional state of an individual to a physiological aspect of the individual at least partially in response to detecting a radiant kinetic energy from the individual of operation 2002 can include operation 2036, that can include but is not limited to, adjusting a temperature in a bed in which the individual is situated at least partially in response to the detecting the radiant kinetic energy from the individual. For example, adjusting a temperature of a bed in which the individual is located, such as for sleeping and/or as a patient. One embodiment of the adjusting a positional state of an individual to a physiological aspect of the individual at least partially in response to detecting a radiant kinetic energy from the individual of operation 2002 can include operation 2038, that can include but is not limited to, delaying adjusting the positional state of the individual at least partially in response to the detecting the radiant kinetic energy from the individual. For example, treating the individual some prescribed duration after monitoring the individual. One embodiment of the adjusting a positional state of an individual to a physiological aspect of the individual at least partially in response to detecting a radiant kinetic energy from the individual of operation 2002 can include operation 2040, that can include but is not limited to, positioning the individual at least partially in response to the detecting the radiant kinetic energy from the individual. For example, shifting the individual (e.g., within a bed, or at other location) such as to limit bed sores, respond to illnesses or injuries, control adverse effects of poor circulation, etc. One embodiment of the adjusting a positional state of an individual to a physiological aspect of the individual at least partially in response to detecting a radiant kinetic energy from the individual of operation 2002 can include operation 2042, that can include but is not limited to, advising the individual to adjust their positional state themselves at least partially in response to the detecting the radiant kinetic energy from the individual. For example, advising the individual to move themselves such as with a vocal, textual, audio, graphical, or other prompt, such as when the individual is in an aircraft, movie, etc. One embodiment of the adjusting a positional state of an individual to a physiological aspect of the individual at least partially in response to detecting a radiant kinetic energy from the individual of operation 2002 can include operation 2044, that can include but is not limited to, distributing temperature related information relating to the individual at least partially in response to the detecting the radiant kinetic energy from the individual. For example, distributing temperature-related information such as can be ascertained using temperature-deriving, infrared, or other mechanism, which may relate to the individual. One embodiment of the adjusting a positional state of an individual to a physiological aspect of the individual at least partially in response to detecting a radiant kinetic energy from the individual of operation 2002 can include operation 2046, that can include but is not limited to, indicating to a caretaker to adjust the positional state of the individual at least partially in response to the detecting the radiant kinetic energy from the individual. For example, indicating to a caretaker, such as a doctor, medical personnel, hospital staff, nursing home staff, etc. radiant kinetic energy of the individual that is monitored and which may be used to treat the individual. The order of the operations, methods, mechanisms, etc. as described with respect to FIG. 13 (including FIGS. 13*a* and 13*b*) is intended to be illustrative in nature, and not limited in scope.

FIG. 12 shows one embodiment of the radiant kinetic energy imager 100 that can be operated to configure or position an individual at least partially in response to a determining at least one physiologically-indicating body temperature of the individual derived at least partially in response to detecting a radiant kinetic energy from the individual. There can be a variety of embodiments of the radiant kinetic energy imager 100 that can be configured, and or operate, similar to as described in this disclosure with respect to FIGS. 1 to 11, for example.

Figure 14A:
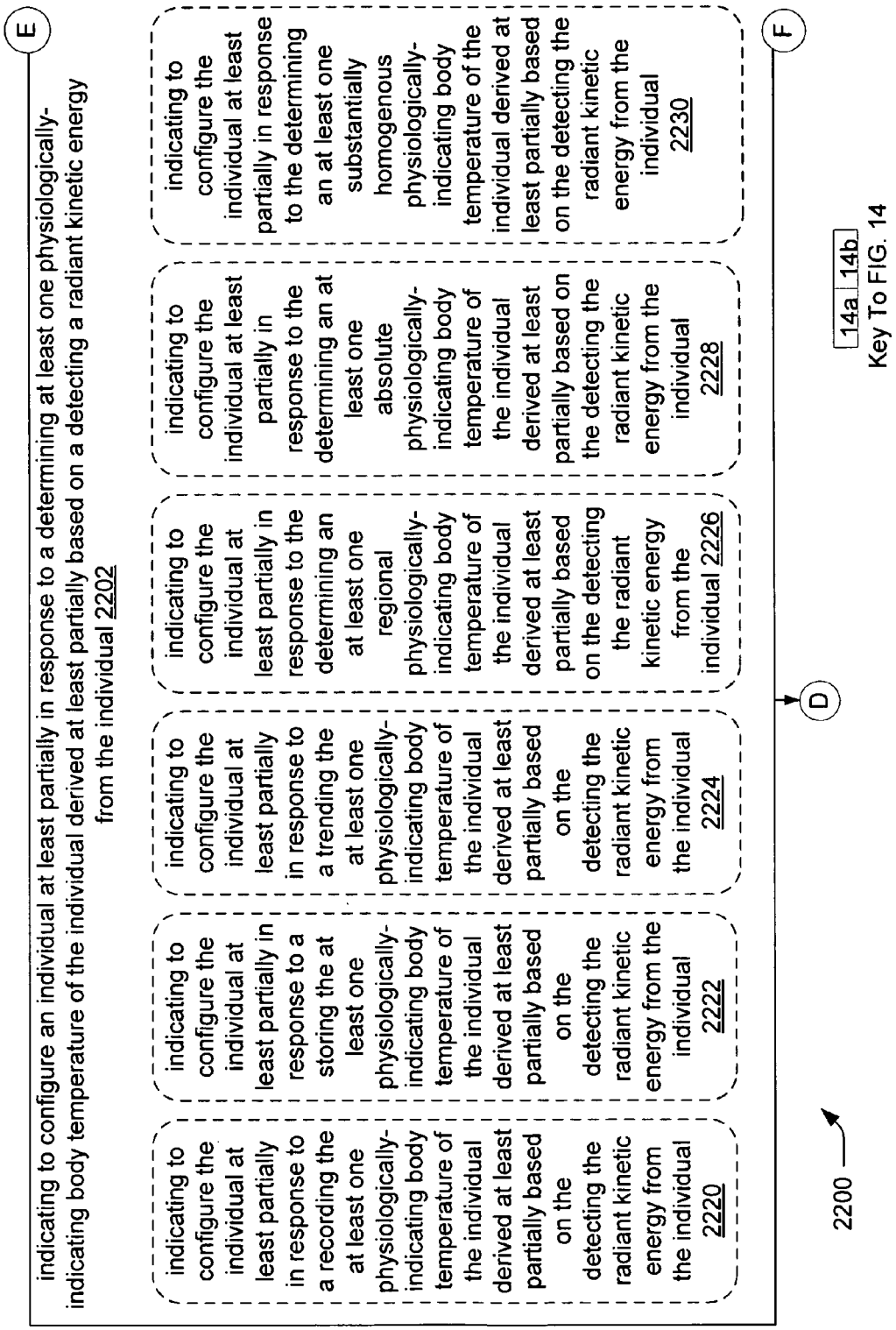
FIGS. 14a and 14b, is a flow chart of another embodiment of a radiant kinetic energy imaging technique which may be effected by certain embodiments of the radiant kinetic energy imager of FIG. 12.
Figure 14B:
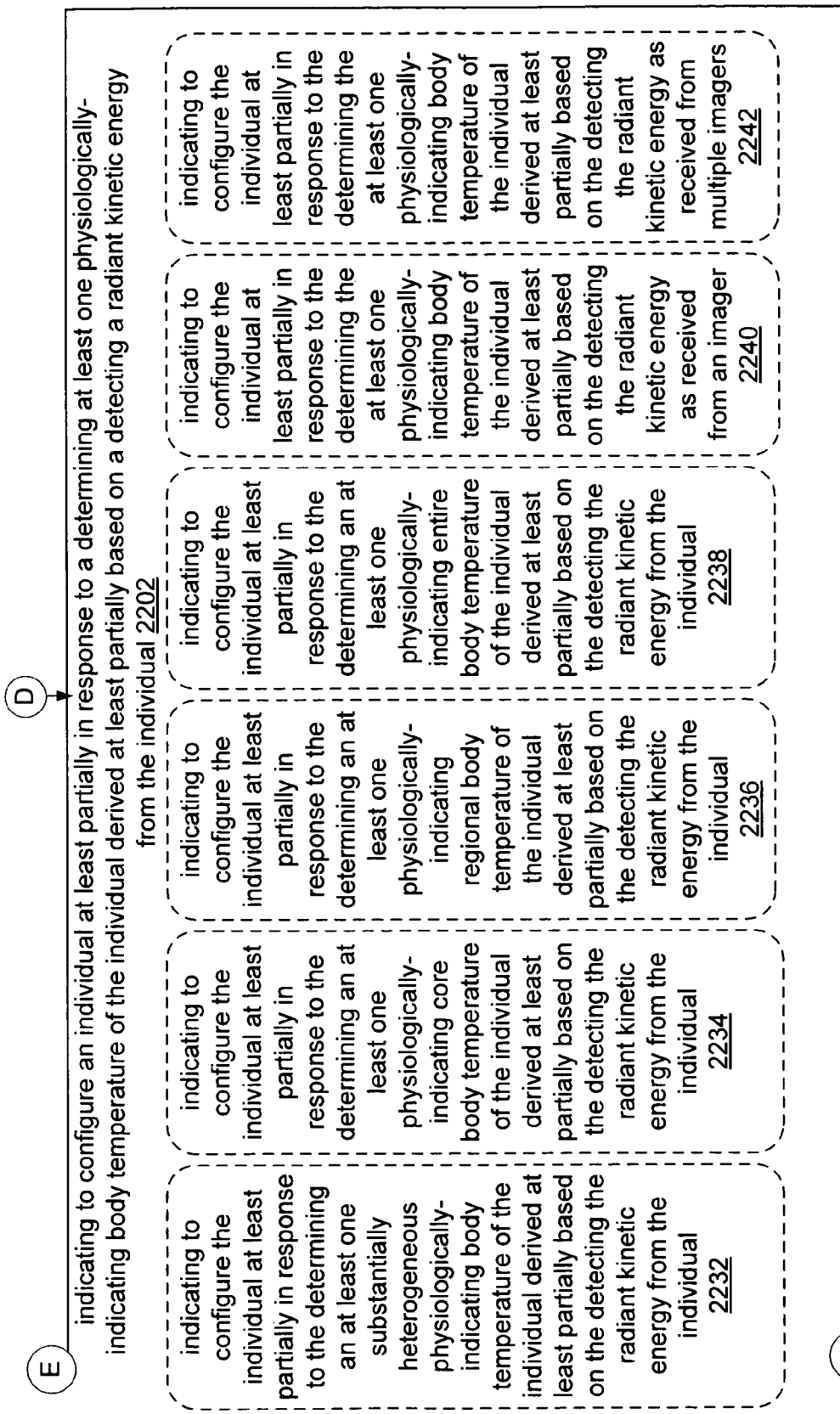

One embodiment of a high-level flowchart of a radiant kinetic energy sensing technique 2200 is described with respect to FIG. 14 (which includes FIGS. 14*a* and 14*b*) and can include, but is not limited to, operation 2202. One embodiment of operation 2202 can include, but is not limited to, operations 2220, 2222, 2224, 2226, 2228, 2230, 2232, 2234, 2236, 2238, 2240, and/or 2242. The high-level flowchart of FIG. 14 (which includes FIGS. 14*a* and 14*b*) should be considered in combination with the embodiments of the radiant kinetic energy imager 100, as described with respect to FIG. 12. One embodiment of operation 2202 can include, but is not limited to, indicating to configure an individual at least partially in response to a determining at least one physiologically-indicating body temperature of the individual derived at least partially based on a detecting a radiant kinetic energy from the individual. For example, positioning the individual (such as with an assistant and/or an automated mechanism) based at least in part on a determining at least one body temperature of the individual at least partially in response to the radiant kinetic energy of the individual, The body temperature can be determined, for example, at least partially by relying at least in part on infrared imaging, etc). One embodiment of the indicating to configure an individual at least partially in response to a determining at least one physiologically-indicating body temperature of the individual derived at least partially based on a detecting a radiant kinetic energy from the individual of operation 2202 can include operation 2220, that can include, but is not limited to, indicating to configure the individual at least partially in response to a recording the at least one physiologically-indicating body temperature of the individual derived at least partially based on the detecting the radiant kinetic energy from the individual. For example, indicating to configure the individual at least partially in response to recording the at least one determined physiologically-indicating body temperature of the individual in a data, textual, graphical, imaged, or other form. One embodiment of the indicating to configure an individual at least partially in response to a determining at least one physiologically-indicating body temperature of the individual derived at least partially based on a detecting a radiant kinetic energy from the individual of operation 2202 can include operation 2222, that can include, but is not limited to, indicating to configure the individual at least partially in response to a storing the at least one physiologically-indicating body temperature of the individual derived at least partially based on the detecting the radiant kinetic energy from the individual. For example, indicating to configure the individual at least partially in response to storing the at least one determined physiologically-indicating body temperature of the individual in a data, textual, graphical, imaged, or other form. One embodiment of the indicating to configure an individual at least partially in response to a determining at least one physiologically-indicating body temperature of the individual derived at least partially based on a detecting a radiant kinetic energy from the individual of operation 2202 can include operation 2224, that can include, but is not limited to, indicating to configure the individual at least partially in response to a trending the at least one physiologically-indicating body temperature of the individual derived at least partially based on the detecting the radiant kinetic energy from the individual. For example, indicating to configure the individual at least partially in response to trending the at least one determined physiologically-indicating body temperature of the individual, such as can be used to determine whether at least one temperature is tending to remain constant, rising, or lowering over time. One embodiment of the indicating to configure an individual at least partially in response to a determining at least one physiologically-indicating body temperature of the individual derived at least partially based on a detecting a radiant kinetic energy from the individual of operation 2202 can include operation 2226, that can include, but is not limited to, indicating to configure the individual at least partially in response to the determining an at least one regional physiologically-indicating body temperature of the individual derived at least partially based on the detecting the radiant kinetic energy from the individual. For example, indicating to configure the individual at least partially in response to determining an at least one regional physiologically-indicating body temperature of the individual. One embodiment of the indicating to configure an individual at least partially in response to a determining at least one physiologically-indicating body temperature of the individual derived at least partially based on a detecting a radiant kinetic energy from the individual of operation 2202 can include operation 2228, that can include, but is not limited to, indicating to configure the individual at least partially in response to the determining an at least one absolute physiologically-indicating body temperature of the individual derived at least partially based on the detecting the radiant kinetic energy from the individual. For example, indicating to configure the individual at least partially in response to determining at least one absolute physiologically-indicating body temperature of the individual (e.g., the temperature on the Fahrenheit or Celsius scale). One embodiment of the indicating to configure an individual at least partially in response to a determining at least one physiologically-indicating body temperature of the individual derived at least partially based on a detecting a radiant kinetic energy from the individual of operation 2202 can include operation 2230, that can include, but is not limited to, indicating to configure the individual at least partially in response to the determining an at least one substantially homogenous physiologically-indicating body temperature of the individual derived at least partially based on the detecting the radiant kinetic energy from the individual. For example, indicating to configure the individual at least partially in response to determining the at least one physiologically-indicating body temperature of the individual in a manner that the temperature is substantially homogenous or uniform across the individual. One embodiment of the indicating to configure an individual at least partially in response to a determining at least one physiologically-indicating body temperature of the individual derived at least partially based on a detecting a radiant kinetic energy from the individual of operation 2202 can include operation 2232, that can include, but is not limited to, indicating to configure the individual at least partially in response to the determining an at least one substantially heterogeneous physiologically-indicating body temperature of the individual derived at least partially based on the detecting the radiant kinetic energy from the individual. For example, indicating to configure the individual at least partially in response to determining the at least one physiologically-indicating body temperature of the individual in a manner that the temperature is substantially heterogeneous or non-uniform at different locations across the individual. One embodiment of the indicating to configure an individual at least partially in response to a determining at least one physiologically-indicating body temperature of the individual derived at least partially based on a detecting a radiant kinetic energy from the individual of operation 2202 can include operation 2234, that can include, but is not limited to, indicating to configure the individual at least partially in response to the determining an at least one physiologically-indicating core body temperature of the individual derived at least partially based on the detecting the radiant kinetic energy from the individual. For example, indicating to configure the individual at least partially in response to determining the core body temperature of the individual, either using one temperature indication; or by averaging, scaling, or otherwise combining multiple physiologically-indicating core body temperatures. One embodiment of the indicating to configure an individual at least partially in response to a determining at least one physiologically-indicating body temperature of the individual derived at least partially based on a detecting a radiant kinetic energy from the individual of operation 2202 can include operation 2236, that can include, but is not limited to, indicating to configure the individual at least partially in response to the determining an at least one physiologically-indicating regional body temperature of the individual derived at least partially based on the detecting the radiant kinetic energy from the individual. For example, indicating to configure the individual at least partially in response to determining the regional body temperature of the individual, which may be an extremity body temperature or other body temperature, either using one temperature indication; or by averaging, scaling, or otherwise combining multiple physiologically-indicating regional body temperatures. One embodiment of the indicating to configure an individual at least partially in response to a determining at least one physiologically-indicating body temperature of the individual derived at least partially based on a detecting a radiant kinetic energy from the individual of operation 2202 can include operation 2238, that can include, but is not limited to, indicating to configure the individual at least partially in response to the determining an at least one physiologically-indicating entire body temperature of the individual derived at least partially based on the detecting the radiant kinetic energy from the individual. For example, indicating to configure the individual at least partially in response to determining a representative entire body temperature of the individual, either using one temperature indication; or by averaging, scaling, or otherwise combining multiple physiologically-indicating entire body temperatures. One embodiment of the indicating to configure an individual at least partially in response to a determining at least one physiologically-indicating body temperature of the individual derived at least partially based on a detecting a radiant kinetic energy from the individual of operation 2202 can include operation 2240, that can include, but is not limited to, indicating to configure the individual at least partially in response to the determining the at least one physiologically-indicating body temperature of the individual derived at least partially based on the detecting the radiant kinetic energy as received from an imager. For example, indicating to configure the individual at least partially in response to determining the at least one physiologically-indicating body temperature of the individual at least partially from only one image such as by using a single radiant kinetic energy sampled image. One embodiment of the indicating to configure an individual at least partially in response to a determining at least one physiologically-indicating body temperature of the individual derived at least partially based on a detecting a radiant kinetic energy from the individual of operation 2202 can include operation 2242, that can include, but is not limited to, indicating to configure the individual at least partially in response to the determining the at least one physiologically-indicating body temperature of the individual derived at least partially based on the detecting the radiant kinetic energy as received from multiple imagers. For example, indicating to configure the individual at least partially in response to determining the at least one physiologically-indicating body temperature of the individual at least partially from multiple images such as by utilizing multiple radiant kinetic energy sampled images, which may be successive. The order of the operations, methods, mechanisms, etc. as described with respect to FIG. 14 (which includes FIGS. 14*a* and 14*b*) is intended to be illustrative in nature, and not limited in scope.

Figure 15:
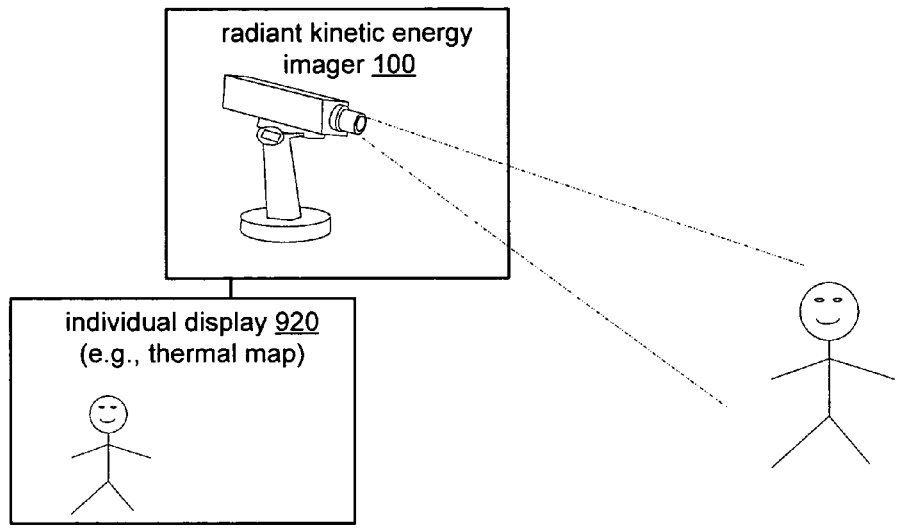
FIG. 15 is a diagram of one embodiment of the radiant kinetic energy imager associated with a display.

FIG. 15 shows one embodiment of the individual display 100 including an individual display 920, as described with respect to FIG. 9, that can be operated to determine a configuration or position of an individual at least partially in response to a determining at least one physiologically-indicating body temperature of the individual derived at least partially in response to detecting a radiant kinetic energy from the individual. There can be a variety of embodiments of the radiant kinetic energy imager 100 that can be configured, and or operate, similar to as described in this disclosure with respect to FIGS. 1 to 11, for example.

Figure 16:
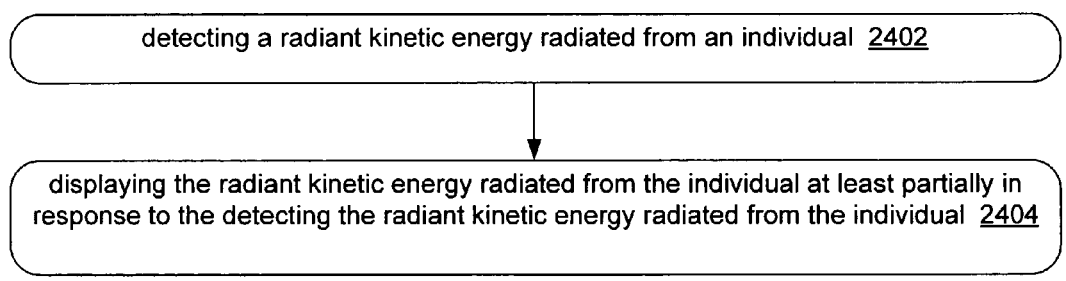
FIG. 16 is a flow chart of another embodiment of a radiant kinetic energy imaging technique which may be affected by certain embodiments of the radiant kinetic energy imager and/or display of FIG. 15.

One embodiment of a high-level flowchart of a radiant kinetic energy display technique 2400 is described with respect to FIG. 16 and can include, but is not limited to, operations 2402 and/or 2404. The high-level flowchart of FIG. 16 should be considered in combination with the embodiments of the radiant kinetic energy imager 100, as well as the individual display 920 of FIG. 15. One embodiment of operation 2402 can include, but is not limited to, detecting a radiant kinetic energy radiated from an individual. For example, utilizing a number of embodiments of the radiant kinetic energy imager 100 as described with respect to FIGS. 1-11 to detect radiant kinetic energy radiated from the individual. One embodiment of operation 2404 can include, but is not limited to, displaying the radiant kinetic energy radiated from the individual at least partially in response to the detecting the radiant kinetic energy radiated from the individual. For example, displaying the detected radiated energy at least partially in response to the detected radiant energy radiated from the individual.

In one or more various aspects, related systems include but are not limited to circuitry and/or programming for effecting the herein-referenced method aspects; the circuitry and/or programming can be virtually any combination of hardware, software, electromechanical system, and/or firmware configurable to effect the herein-referenced method aspects depending upon the design choices of the system designer.

4. Conclusion

This disclosure provides a number of embodiments of the radiant kinetic energy imager. The embodiments of the radiant kinetic energy imager 100 as described with respect to this disclosure are intended to be illustrative in nature, and are not limiting its scope.

Those having skill in the art will recognize that the state of the art in computer, controller, communications, networking, and other similar technologies has progressed to the point where there is little distinction left between hardware, firmware, and/or software implementations of aspects of systems, such as may be utilized in the radiant kinetic energy imager. The use of hardware, firmware, and/or software can therefore generally represent (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle can vary with the context in which the processes and/or systems and/or other technologies are deployed. For example, if an implementer determines that speed and accuracy are paramount, the implementer and/or designer of the radiant kinetic energy imager may opt for mainly a hardware and/or firmware vehicle. In alternate embodiments, if flexibility is paramount, the implementer and/or designer may opt for mainly a software implementation. In yet other embodiments, the implementer and/or designer may opt for some combination of hardware, software, and/or firmware. Hence, there are several possible techniques by which the processes and/or devices and/or other technologies described herein may be effected, none of which is inherently superior to the other in that any vehicle to be utilized is a choice dependent upon the context in which the vehicle can be deployed and the specific concerns (e.g., speed, flexibility, or predictability) of the implementer, any of which may vary.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. Certain embodiments of the radiant kinetic energy imager 100 can even be controlled utilizing mechanical, or electro-mechanical systems. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

All of the above U.S. patents, U.S. patent application publications, U.S. patent applications, foreign patents, foreign patent applications and non-patent publications referred to in this specification and/or listed in any Application Data Sheet, are incorporated herein by reference, in their entireties.

It is to be understood by those skilled in the art that, in general, that the terms used in the disclosure, including the drawings and the appended claims (and especially as used in the bodies of the appended claims), are generally intended as "open" terms. For example, the term "including" should be interpreted as "including but not limited to"; the term "having" should be interpreted as "having at least"; and the term "includes" should be interpreted as "includes, but is not limited to"; etc. In this disclosure and the appended claims, the terms "a", "the", and "at least one" positioned prior to one or more goods, items, and/or services are intended to apply inclusively to either one or a plurality of those goods, items, and/or services.

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that could have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that could have A alone, B alone, C alone, A and B together, A and C together, B and C together, and/or A, B, and C together, etc.).

Those skilled in the art will appreciate that the herein-described specific exemplary processes and/or devices and/or technologies are representative of more general processes and/or devices and/or technologies taught elsewhere herein, such as in the claims filed herewith and/or elsewhere in the present application.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method, comprising:
adjusting a positional state of an individual based at least in part on an electronic output of an indication related to the adjusting the positional state of the individual, the electronic output generated at least in part in response to electronically detecting a physiological aspect other than the positional state of the individual.

2. The method of claim 1, wherein the adjusting a positional state of an individual based at least in part on an electronic output of an indication related to the adjusting the positional state of the individual, the electronic output generated at least in part in response to electronically detecting a physiological aspect other than the positional state of the individual further comprises:
   notifying the individual according to the one or more physiological aspects other than solely the positional state of the individual at least partially in response to detecting radiant energy from the individual.

3. The method of claim 1, wherein the adjusting a positional state of an individual based at least in part on an electronic output of an indication related to the adjusting the positional state of the individual, the electronic output generated at least in part in response to electronically detecting a physiological aspect other than the positional state of the individual further comprises:
   treating health related aspects of the individual at least partially in response to detecting radiant energy from the individual.

4. The method of claim 1, wherein the adjusting a positional state of an individual based at least in part on an electronic output of an indication related to the adjusting the positional state of the individual, the electronic output generated at least in part in response to electronically detecting a physiological aspect other than the positional state of the individual further comprises:
   adjusting the positional state of the individual according to the one or more physiological aspects other than solely the positional state of the individual at least partially in response to detecting radiant energy from the individual at least partially using a radiant energy imager.

5. The method of claim 1, wherein the adjusting a positional state of an individual based at least in part on an electronic output of an indication related to the adjusting the positional state of the individual, the electronic output generated at least in part in response to electronically detecting a physiological aspect other than the positional state of the individual further comprises:
   adjusting the positional state of the individual according to the one or more physiological aspects other than solely the positional state of an immobile individual at least partially in response to detecting radiant energy from the immobile individual.

6. The method of claim 1, wherein the adjusting a positional state of an individual based at least in part on an electronic output of an indication related to the adjusting the positional state of the individual, the electronic output generated at least in part in response to electronically detecting a physiological aspect other than the positional state of the individual further comprises:
   adjusting the positional state of the individual according to the one or more physiological aspects other than solely the positional state of an inactive individual at least partially in response to detecting radiant energy from the inactive individual.

7. The method of claim 1, wherein the adjusting a positional state of an individual based at least in part on an electronic output of an indication related to the adjusting the positional state of the individual, the electronic output generated at least in part in response to electronically detecting a physiological aspect other than the positional state of the individual further comprises:
   adjusting a temperature in a room in which the individual is situated at least partially in response to detecting radiant energy from the individual.

8. The method of claim 1, wherein the adjusting a positional state of an individual based at least in part on an electronic output of an indication related to the adjusting the positional state of the individual, the electronic output generated at least in part in response to electronically detecting a physiological aspect other than the positional state of the individual further comprises:
   changing a treatment at least partially in response to detecting radiant energy from the individual.

9. The method of claim 1, wherein the adjusting a positional state of an individual based at least in part on an electronic output of an indication related to the adjusting the positional state of the individual, the electronic output generated at least in part in response to electronically detecting a physiological aspect other than the positional state of the individual further comprises:
   adjusting a temperature in a bed in which the individual is situated at least partially in response to detecting radiant energy from the individual.

10. The method of claim 1, wherein the adjusting a positional state of an individual based at least in part on an electronic output of an indication related to the adjusting the positional state of the individual, the electronic output generated at least in part in response to electronically detecting a physiological aspect other than the positional state of the individual further comprises:
    delaying adjusting the positional state of the individual at least partially in response to detecting radiant energy from the individual.

11. The method of claim 1, wherein the adjusting a positional state of an individual based at least in part on an electronic output of an indication related to the adjusting the positional state of the individual, the electronic output generated at least in part in response to electronically detecting a physiological aspect other than the positional state of the individual further comprises:
    advising the individual to adjust their positional state themselves at least partially in response to detecting radiant energy from the individual.

12. The method of claim 1, wherein the adjusting a positional state of an individual based at least in part on an electronic output of an indication related to the adjusting the positional state of the individual, the electronic output generated at least in part in response to electronically detecting a physiological aspect other than the positional state of the individual further comprises:
    distributing temperature related information relating to the individual at least partially in response to detecting radiant energy from the individual.

13. The method of claim 1, wherein the adjusting a positional state of an individual based at least in part on an electronic output of an indication related to the adjusting the positional state of the individual, the electronic output generated at least in part in response to electronically detecting a physiological aspect other than the positional state of the individual further comprises:
    indicating to a caretaker to adjust the positional state of the individual at least partially in response to detecting radiant energy from the individual.

14. A method, comprising:
    electronically indicating to reposition one or more portions of an individual at least partially in response to electronically determining a physiological status of the individual other than positional status of the individual.

15. The method of claim 14, wherein the electronically indicating to reposition one or more portions of an individual at least partially in response to electronically determining a physiological status of the individual other than positional status of the individual comprises:
   indicating to configure the individual at least partially in response to a recording at least one physiologically-indicating body temperature of the individual derived at least partially based on detecting the radiant energy from the individual.

16. The method of claim 14, wherein the electronically indicating to reposition one or more portions of an individual at least partially in response to electronically determining a physiological status of the individual other than positional status of the individual comprises:
   indicating to configure the individual at least partially in response to a storing at least one physiologically-indicating body temperature of the individual derived at least partially based on detecting the radiant energy from the individual.

17. The method of claim 14, wherein the electronically indicating to reposition one or more portions of an individual at least partially in response to electronically determining a physiological status of the individual other than positional status of the individual comprises:
   indicating to configure the individual at least partially in response to a trending of at least one physiologically-indicating body temperature of the individual derived at least partially based on detecting the radiant energy from the individual.

18. The method of claim 14, wherein the electronically indicating to reposition one or more portions of an individual at least partially in response to electronically determining a physiological status of the individual other than positional status of the individual comprises:
   indicating to configure the individual at least partially in response to determining an at least one absolute physiologically-indicating body temperature of the individual derived at least partially based on detecting the radiant energy from the individual.

19. The method of claim 14, wherein the electronically indicating to reposition one or more portions of an individual at least partially in response to electronically determining a physiological status of the individual other than positional status of the individual comprises:
   indicating to configure the individual at least partially in response to determining an at least one substantially homogenous physiologically-indicating body temperature of the individual derived at least partially based on detecting the radiant energy from the individual.

20. The method of claim 14, wherein the electronically indicating to reposition one or more portions of an individual at least partially in response to electronically determining a physiological status of the individual other than positional status of the individual comprises:
   indicating to configure the individual at least partially in response to determining an at least one substantially heterogeneous physiologically-indicating body temperature of the individual derived at least partially based on detecting the radiant energy from the individual.

21. The method of claim 14, wherein the electronically indicating to reposition one or more portions of an individual at least partially in response to electronically determining a physiological status of the individual other than positional status of the individual comprises:
   indicating to configure the individual at least partially in response to determining an at least one physiologically-indicating core body temperature of the individual derived at least partially based on detecting the radiant energy from the individual.

22. The method of claim 14, wherein the electronically indicating to reposition one or more portions of an individual at least partially in response to electronically determining a physiological status of the individual other than positional status of the individual comprises:
   indicating to configure the individual at least partially in response to determining an at least one physiologically-indicating regional body temperature of the individual derived at least partially based on detecting the radiant energy from the individual.

23. The method of claim 14, wherein the electronically indicating to reposition one or more portions of an individual at least partially in response to electronically determining a physiological status of the individual other than positional status of the individual comprises:
   indicating to configure the individual at least partially in response to determining an at least one physiologically-indicating entire body temperature of the individual derived at least partially based on detecting the radiant energy from the individual.

24. The method of claim 14, wherein the electronically indicating to reposition one or more portions of an individual at least partially in response to electronically determining a physiological status of the individual other than positional status of the individual comprises:
   indicating to configure the individual at least partially in response to determining at least one physiologically-indicating body temperature of the individual derived at least partially based on the detecting the radiant energy as received from an imager.

25. The method of claim 14, wherein the electronically indicating to reposition one or more portions of an individual at least partially in response to electronically determining a physiological status of the individual other than positional status of the individual comprises:
   indicating to configure the individual at least partially in response to determining the at least one physiologically-indicating body temperature of the individual derived at least partially based on detecting the radiant energy as received from multiple imagers.

26. An apparatus, comprising:
   an at least one radiant energy imager configurable to detect a radiant energy from an individual and configurable to adjust a positional state of the individual based at least in part on a physiological aspect of the individual at least partially in response to the at least one radiant energy imager detecting a radiant energy from the individual.

27. The apparatus of claim 26, wherein the at least one radiant energy imager configurable to detect a radiant energy from an individual and configurable to adjust a positional state of the individual based at least in part on a physiological aspect of the individual at least partially in response to the at least one radiant energy imager detecting a radiant energy from the individual further comprises:
   the at least one radiant energy imager configurable to adjust the positional state of the individual to signal the physiological aspect of the individual at least partially in response to the at least one radiant energy imager detecting the radiant energy from the individual.

28. The apparatus of claim 26, wherein the at least one radiant energy imager configurable to detect a radiant energy from an individual and configurable to adjust a positional state of the individual based at least in part on a physiological aspect of the individual at least partially in response to the at least one radiant energy imager detecting a radiant energy from the individual further comprises:

the at least one radiant energy imager configurable to adjust the positional state of the individual to notify the physiological aspect of the individual at least partially in response to the at least one radiant energy imager detecting the radiant energy from the individual.

29. The apparatus of claim 26, wherein the at least one radiant energy imager configurable to detect a radiant energy from an individual and configurable to adjust a positional state of the individual based at least in part on a physiological aspect of the individual at least partially in response to the at least one radiant energy imager detecting a radiant energy from the individual further comprises:

the at least one radiant energy imager configurable to adjust the positional state of the individual to treat health related aspects of the individual at least partially in response to the at least one radiant energy imager detecting the radiant energy from the individual.

30. The apparatus of claim 26, wherein the at least one radiant energy imager configurable to detect a radiant energy from an individual and configurable to adjust a positional state of the individual based at least in part on a physiological aspect of the individual at least partially in response to the at least one radiant energy imager detecting a radiant energy from the individual further comprises:

the at least one radiant energy imager configurable to adjust the positional state of the individual to the physiological aspect of an immobile individual at least partially in response to the at least one radiant energy imager detecting the radiant energy from the immobile individual.

31. The apparatus of claim 26, wherein the at least one radiant energy imager configurable to detect a radiant energy from an individual and configurable to adjust a positional state of the individual based at least in part on a physiological aspect of the individual at least partially in response to the at least one radiant energy imager detecting a radiant energy from the individual further comprises:

the at least one radiant energy imager configurable to adjust the positional state of the individual to the physiological aspect of an inactive individual at least partially in response to the at least one radiant energy imager detecting the radiant energy from the inactive individual.

32. The apparatus of claim 26, wherein the at least one radiant energy imager configurable to detect a radiant energy from an individual and configurable to adjust a positional state of the individual based at least in part on a physiological aspect of the individual at least partially in response to the at least one radiant energy imager detecting a radiant energy from the individual further comprises:

the at least one radiant energy imager configurable to adjust a temperature in a room in which the individual is situated at least partially in response to the at least one radiant energy imager detecting the radiant energy from the individual.

33. The apparatus of claim 26, wherein the at least one radiant energy imager configurable to detect a radiant energy from an individual and configurable to adjust a positional state of the individual based at least in part on a physiological aspect of the individual at least partially in response to the at least one radiant energy imager detecting a radiant energy from the individual further comprises:

the at least one radiant energy imager configurable to change a treatment at least partially in response to the at least one radiant energy imager detecting the radiant energy from the individual.

34. The apparatus of claim 26, wherein the at least one radiant energy imager configurable to detect a radiant energy from an individual and configurable to adjust a positional state of the individual based at least in part on a physiological aspect of the individual at least partially in response to the at least one radiant energy imager detecting a radiant energy from the individual further comprises:

the at least one radiant energy imager configurable to adjust a temperature in a bed in which the individual is situated at least partially in response to the at least one radiant energy imager detecting the radiant energy from the individual.

35. The apparatus of claim 26, wherein the at least one radiant energy imager configurable to detect a radiant energy from an individual and configurable to adjust a positional state of the individual based at least in part on a physiological aspect of the individual at least partially in response to the at least one radiant energy imager detecting a radiant energy from the individual further comprises:

the at least one radiant energy imager configurable to delay adjusting the positional state of the individual at least partially in response to the at least one radiant energy imager detecting the radiant energy from the individual.

36. The apparatus of claim 26, wherein the at least one radiant energy imager configurable to detect a radiant energy from an individual and configurable to adjust a positional state of the individual based at least in part on a physiological aspect of the individual at least partially in response to the at least one radiant energy imager detecting a radiant energy from the individual further comprises:

the at least one radiant energy imager configurable to position the individual at least partially in response to the at least one radiant energy imager detecting the radiant energy from the individual.

37. The apparatus of claim 26, wherein the at least one radiant energy imager configurable to detect a radiant energy from an individual and configurable to adjust a positional state of the individual based at least in part on a physiological aspect of the individual at least partially in response to the at least one radiant energy imager detecting a radiant energy from the individual further comprises:

the at least one radiant energy imager configurable to advise the individual to move themselves at least partially in response to the at least one radiant energy imager detecting the radiant energy from the individual.

38. The apparatus of claim 26, wherein the at least one radiant energy imager configurable to detect a radiant energy from an individual and configurable to adjust a positional state of the individual based at least in part on a physiological aspect of the individual at least partially in response to the at least one radiant energy imager detecting a radiant energy from the individual further comprises:

the at least one radiant energy imager configurable to distribute temperature related information relating to the individual at least partially in response to the at least one radiant energy imager detecting the radiant energy from the individual.

39. An apparatus, comprising:

an at least one radiant energy imager operable to configure an individual at least partially in response to a determining at least one physiologically-indicating body temperature of the individual at least partially based on the at least one radiant energy imager detecting a radiant energy from the individual.

40. The apparatus of claim 39, wherein the at least one radiant energy imager operable to configure an individual at least partially in response to a determining at least one physiologically-indicating body temperature of the individual at least partially based on the at least one radiant energy imager detecting a radiant energy from the individual comprises:

the at least one radiant energy imager operable to record the at least one physiologically-indicating body temperature of the individual at least partially based on the at least one radiant energy imager detecting the radiant energy from the individual.

41. The apparatus of claim 39, wherein the at least one radiant energy imager operable to configure an individual at least partially in response to a determining at least one physiologically-indicating body temperature of the individual at least partially based on the at least one radiant energy imager detecting a radiant energy from the individual comprises:

the at least one radiant energy imager operable to store the at least one physiologically-indicating body temperature of the individual at least partially based on the at least one radiant energy imager detecting the radiant energy from the individual.

42. The apparatus of claim 39, wherein the at least one radiant energy imager operable to configure an individual at least partially in response to a determining at least one physiologically-indicating body temperature of the individual at least partially based on the at least one radiant energy imager detecting a radiant energy from the individual comprises:

the at least one radiant energy imager operable to configure the individual at least partially in response to the at least one radiant energy imager determining an at least one regional physiologically-indicating body temperature of the individual at least partially based on the at least one radiant energy imager detecting the radiant energy from the individual.

43. The apparatus of claim 39, wherein the at least one radiant energy imager operable to configure an individual at least partially in response to a determining at least one physiologically-indicating body temperature of the individual at least partially based on the at least one radiant energy imager detecting a radiant energy from the individual comprises:

the at least one radiant energy imager operable to configure the individual at least partially in response to the at least one radiant energy imager determining an at least one absolute physiologically-indicating body temperature of the individual at least partially based on the detecting the radiant energy from the individual.

44. The apparatus of claim 39, wherein the at least one radiant energy imager operable to configure an individual at least partially in response to a determining at least one physiologically-indicating body temperature of the individual at least partially based on the at least one radiant energy imager detecting a radiant energy from the individual comprises:

the at least one radiant energy imager operable to configure the individual at least partially in response to the at least one radiant energy imager determining an at least one substantially homogenous physiologically-indicating body temperature of the individual at least partially based on the at least one radiant energy imager detecting the radiant energy from the individual.

45. The apparatus of claim 39, wherein the at least one radiant energy imager operable to configure an individual at least partially in response to a determining at least one physiologically-indicating body temperature of the individual at least partially based on the at least one radiant energy imager detecting a radiant energy from the individual comprises:

the at least one radiant energy imager operable to configure the individual at least partially in response to the at least one radiant energy imager determining an at least one substantially heterogeneous physiologically-indicating body temperature of the individual at least partially based on the at least one radiant energy imager detecting the radiant energy from the individual.

46. The apparatus of claim 39, wherein the at least one radiant energy imager operable to configure an individual at least partially in response to a determining at least one physiologically-indicating body temperature of the individual at least partially based on the at least one radiant energy imager detecting a radiant energy from the individual comprises:

the at least one radiant energy imager operable to configure the individual at least partially in response to the at least one radiant energy imager determining an at least one physiologically-indicating core body temperature of the individual at least partially based on the at least one radiant energy imager detecting the radiant energy from the individual.

47. The apparatus of claim 39, wherein the at least one radiant energy imager operable to configure an individual at least partially in response to a determining at least one physiologically-indicating body temperature of the individual at least partially based on the at least one radiant energy imager detecting a radiant energy from the individual comprises:

the at least one radiant energy imager operable to configure the individual at least partially in response to the at least one radiant energy imager determining an at least one physiologically-indicating regional body temperature of the individual at least partially based on the at least one radiant energy imager detecting the radiant energy from the individual.

48. The apparatus of claim 39, wherein the at least one radiant energy imager operable to configure an individual at least partially in response to a determining at least one physiologically-indicating body temperature of the individual at least partially based on the at least one radiant energy imager detecting a radiant energy from the individual comprises:

the at least one radiant energy imager operable to configure the individual at least partially in response to the at least one radiant energy imager determining an at least one physiologically-indicating entire body temperature of the individual at least partially based on the at least one radiant energy imager detecting the radiant energy from the individual.

49. The apparatus of claim 39, wherein the at least one radiant energy imager operable to configure an individual at least partially in response to a determining at least one physiologically-indicating body temperature of the individual at least partially based on the at least one radiant energy imager detecting a radiant energy from the individual comprises:

the at least one radiant energy imager operable to configure the individual at least partially in response to the at least one radiant energy imager determining the at least one physiologically-indicating body temperature of the individual at least partially based on the at least one radiant energy imager detecting the radiant energy as received from an imager.

50. The apparatus of claim 39, wherein the at least one radiant energy imager operable to configure an individual at least partially in response to a determining at least one physiologically-indicating body temperature of the individual at least partially based on the at least one radiant energy imager detecting a radiant energy from the individual comprises:

the at least one radiant energy imager operable to configure the individual at least partially in response to the at least one radiant energy imager determining the at least one physiologically-indicating body temperature of the individual at least partially based on the at least one radiant energy imager detecting the radiant energy as received from multiple imagers.

51. A system, comprising:

an electromechanical positional adjustment component configurable to adjust a positional state of an individual in response to at least in part a determining of a physiological aspect of the individual apart from determining positional aspects of the individual based at least partially on a detected radiant energy from the individual.

* * * * *